United States Patent
Saebo et al.

(10) Patent No.: US 8,207,225 B2
(45) Date of Patent: *Jun. 26, 2012

(54) CONJUGATED LINOLEIC ACID COMPOSITIONS

(75) Inventors: Asgeir Saebo, Eidsnes (NO); Carl Skarie, Aberdeen, SD (US)

(73) Assignee: Aker Biomarine ASA, Oslo (NO)

( * ) Notice: Subject to any disclaimer, the term of this patent is extended or adjusted under 35 U.S.C. 154(b) by 822 days.

This patent is subject to a terminal disclaimer.

(21) Appl. No.: 12/020,820

(22) Filed: Jan. 28, 2008

(65) Prior Publication Data

US 2008/0200706 A1    Aug. 21, 2008

Related U.S. Application Data

(63) Continuation of application No. 09/544,004, filed on Apr. 6, 2000, now abandoned, which is a continuation-in-part of application No. 09/132,593, filed on Aug. 11, 1998, now Pat. No. 7,078,051, and a continuation-in-part of application No. 09/270,940, filed on Mar. 17, 1999, now Pat. No. 6,410,761, which is a continuation-in-part of application No. 09/042,767, filed on Mar. 17, 1998, now Pat. No. 6,015,833, and a continuation-in-part of application No. 09/042,538, filed on Mar. 17, 1998, now abandoned.

(51) Int. Cl.
*A61K 31/20* (2006.01)
*A61K 47/00* (2006.01)

(52) U.S. Cl. .................. 514/560; 424/439
(58) Field of Classification Search .............. 424/426, 424/439; 514/560
See application file for complete search history.

(56) References Cited

U.S. PATENT DOCUMENTS

| | | | |
|---|---|---|---|
| 2,242,230 A | 5/1941 | Burr | |
| 2,343,644 A | 3/1944 | Crawley | |
| 2,350,583 A | 6/1944 | Bradley | |
| 3,162,658 A | 12/1964 | Baltes et al. | |
| 3,278,567 A | 10/1966 | Rathjen et al. | |
| 3,729,379 A | 4/1973 | Emken | |
| 4,164,505 A | 8/1979 | Krajca | |
| 4,381,264 A | 4/1983 | Struve | |
| 4,734,226 A | 3/1988 | Parker | |
| 5,017,614 A | 5/1991 | Pariza et al. | |

(Continued)

FOREIGN PATENT DOCUMENTS

DE    19718245    7/1998

(Continued)

OTHER PUBLICATIONS

Arcos et al., 1998, "Rapid Enzymatic Production of acylglycerols from conjugated Linoleic acid and glycerol in the solvent-free system", Biotechnology Letters 20:617.

(Continued)

*Primary Examiner* — Shengjun Wang
(74) *Attorney, Agent, or Firm* — Casimir Jones SC

(57) ABSTRACT

Novel compositions containing conjugated linoleic acids are efficacious as animal feed additives and human dietary supplements. Linoleic acid is converted to its conjugated forms in which the resulting composition is low in certain unusual isomers compared to conventional conjugated linoleic products. In addition, the inventions provides compositions that are prepared according to a novel method that controls oxidation of CLA into volatile organic compounds as well as containing metal oxidant chelators to control oxidation during storage.

38 Claims, 2 Drawing Sheets

U.S. PATENT DOCUMENTS

| | | | |
|---|---|---|---|
| 5,070,104 A | 12/1991 | Pariza et al. | |
| 5,208,356 A | 5/1993 | Pariza et al. | |
| 5,288,619 A | 2/1994 | Brown et al. | |
| 5,428,072 A | 6/1995 | Cook et al. | |
| 5,430,066 A | 7/1995 | Cook et al. | |
| 5,468,887 A | 11/1995 | Gupta | |
| 5,554,646 A | 9/1996 | Cook et al. | |
| 5,585,400 A | 12/1996 | Cook et al. | |
| 5,674,901 A | 10/1997 | Cook et al. | |
| 5,725,873 A | 3/1998 | Cook et al. | |
| 5,760,082 A * | 6/1998 | Cook et al. | 514/560 |
| 5,760,083 A | 6/1998 | Cook et al. | |
| 5,804,210 A | 9/1998 | Cook et al. | |
| 5,814,663 A | 9/1998 | Cook et al. | |
| 5,827,885 A | 10/1998 | Cook et al. | |
| 5,851,572 A | 12/1998 | Cook et al. | |
| 5,855,917 A | 1/1999 | Cook et al. | |
| 5,856,149 A | 1/1999 | Pariza et al. | |
| 5,885,594 A | 3/1999 | Nilsen et al. | |
| 5,914,346 A | 6/1999 | Cook et al. | |
| 5,986,116 A | 11/1999 | Iwata et al. | |
| 6,015,833 A | 1/2000 | Saebo et al. | |
| 6,034,132 A * | 3/2000 | Remmereit | 514/560 |
| 6,159,525 A * | 12/2000 | Lievense et al. | 426/603 |
| 6,160,140 A | 12/2000 | Bhaggan et al. | |
| 6,184,009 B1 | 2/2001 | Cain et al. | |
| 6,225,486 B1 | 5/2001 | Saebo et al. | |
| 6,271,404 B1 | 8/2001 | Bhaggan et al. | |
| 6,524,527 B2 * | 2/2003 | Fimreite et al. | 426/648 |
| 7,029,691 B1 * | 4/2006 | Saebo et al. | 424/439 |
| 7,078,051 B1 * | 7/2006 | Saebo et al. | 424/439 |
| 7,452,548 B1 * | 11/2008 | Saebo et al. | 424/439 |
| 7,776,353 B1 * | 8/2010 | Saebo et al. | 424/439 |
| 2001/0023259 A1 | 9/2001 | Slabas et al. | |

FOREIGN PATENT DOCUMENTS

| | | |
|---|---|---|
| DE | 199 14 279 C1 | 3/1999 |
| DE | 199 22 942 A1 | 5/1999 |
| DE | 199 40 751 A1 | 8/1999 |
| DE | 199 40 752 A1 | 8/1999 |
| EP | 0839897 | 10/1997 |
| EP | 0902082 | 3/1999 |
| EP | 0936266 | 8/1999 |
| EP | 0950410 | 12/2000 |
| EP | 779033 | 9/2001 |
| GB | 558881 | 1/1944 |
| GB | 2179234 | 3/1987 |
| WO | 90/09110 | 8/1990 |
| WO | 92/11768 | 7/1992 |
| WO | 96/34855 | 11/1996 |
| WO | 97/18320 | 5/1997 |
| WO | WO 9718320 A1 * | 5/1997 |
| WO | 97/37546 | 10/1997 |
| WO | 97/38137 | 10/1997 |
| WO | 97/46118 | 12/1997 |
| WO | 97/46230 | 12/1997 |
| WO | 98/05318 | 2/1998 |
| WO | 98/05319 | 2/1998 |
| WO | 98/49129 | 5/1998 |
| WO | 99/32105 | 7/1999 |
| WO | 01/44485 | 6/2001 |
| WO | 01/53512 | 7/2001 |
| WO | 01/77271 | 10/2001 |

OTHER PUBLICATIONS

Banni et al., 2001, J Lipid Research, 42:1056.
Belury, 1995, "Conjugated Dienoic Linoleate: A Polyunsaturated Fatty Acid with Unique Chemoprotective Properties", Nut. Rev. 53(4):83-9.
Berdeau et al, 1998, "A Simply Method of Preparation of Methyl trans-10,cis-12 and cis-9, trans-11-Octadecadienoates from Methyl Linoleate", JAOCS, 75:1749-1755.
Birt et al., 1992, Cancer Res. 52:2035-s.
Blankson et al., 2000, Am. Soc Nutri. Sci. 1-6.
Bradley et al., 1942, "Alkali-Induced Isomerization of Drying Oils and Fatty Acids", Ind. Eng. Chem. 34(2):237-242.
Bretillon et al., 1999, Lipids, 34:965.
Chin et al., 1992, "Dietary Sources of Conjugated Dienoic Isomers of Linoleic Acids, a Newly Recognized Class of Anticarcinogens", J. Food. Comp. Anal, 5:185-197.
Chin et al., 1994, J. Nutrition 124:694.
Christie et al., 1997, "Isomers in Commercial Samples of Conjugated Linoleic Acid", JAOCS, 74(11):1231.
Chuang et al., 2001, Lipids, 36:139.
Cowan, 1950, "Isomerization and Trans-Esterifiation", Jaocs 72:492-99.
Decision of the Technical Board of Appeal European Patent Office; in re EP Patent Application Serial No. 97118467.6; Publication No. 0839897; Applicatnt: Rinoru Oil Mills Co., Ltd.; Dated Nov. 11, 2005; pp. 1-17.
Dugan et al., 1997, "The Effect of Conjugated Linoleic Acid on Fat to Lean Repartitioning and Feed Conversion in Pigs", Canadian Journal of Animal Science. 77: 723-725.
Ha et al., 1991, Cancer Res. 50:1097.
Haraldsson et al., 1991, Acta Chem Scanned 45:723.
Holman et al., 1991, "Unusual Isomeric Polyunsaturated Fatty Acids in Liver Phospholipids of Rats Fed Hydrogenated Oil", PNAS 88:4830-34.
Hudtwalcker & Co. AS Technical Data Sheet, exact publication date unknown.
Ip, 1997, Am. J. Clin. Nutr. 66(6):1523s.
Janssen et al., 1988, Biomedical and Environ. Mass Spectrometry, 16:1-6.
Jie et al., 1997, "High-Resolution Nuclear Magnetic Resonance Spectroscopy—Amplification to Fatty Acids and Tnacylglycerols", Lipids, 32(10):1019-34.
Jie et al., 1997, "Synthesis and Nuclear Magnetic Resonance Properties of All Geometrical Isomers of Conjugated Linoleic Acids", Lipids 32(10):1041-1044.
Kepler et al., 1966, J Biol. Chem. 241:1350-54.
Lipid Technology Newsletter, Peter J. Barnes, Ed., vol. 4, No. 5, pp. 85-86 (Oct. 1998).
Matreya Catalog, 1997, pp. 33-34.
Monster, 2007, "Conjugation of Safflower oil according to example II from patent EP0902082A", Lipid Nutrition Report, pp. 1-3.
Natural Lipids Ltd. AS Technical Data Sheet, Jan. 20, 1997.
P.W. Parodi, 1997, J. Nutr. 127(6):1055-60.
Park, 1999, Lipids, 34:235-241.
Park et al., 1997, "Effect of Conjugated Linoleic Acid on Body Composition in Mice", Lipids, 32(8): 853-58.
Quinn et al., 1998, "A Comparison of Modified Tall Oil and Conjugated Linoleic Acid on Growing-Finishing Pig Growth Performance and Carcass Characteristics", Kansas State University and Lonza, Inc., Midwest Animal Sciences Meeting, Abstract 128:61.
Radlove et al., 1946, "Catalytic Isomerization of Vegetable Oils", Ind. Eng. Chem, 38(10):997-1002.
Ron Udell, Information About Conjugated Linoleic Acid, published by Soft Gel Technologies Incorporated.
Scholfield and Koritalia, 1970, "A Simple Method for Preparation of Methyl Trans-10,cis-12 Octadecadienoate", JOACS 47(8):303.
Sebedio et al., 1988, "Linoleic Acid Isomers in Heat Treated Sunflower Oils", JAOCS 65(3):362-366.
Sebedio et al., 1997, "Metabolites of Conjugated Isomers of Linoleic Acid (CLA) in the Rat", Biochem Biophys. Acta, 1345:5-10.
Sebedio et al., 1999, Lipids, 34:1319-1325.
Sehat et al., 1998, "Silver-Ion High-Performance Liquid Chromatographic Separation and Identification of Conjugated Linoleic Acid Isomers", Lipids, 33(2):217-21.
Sehat et al., 1999, "Improved Separation of Conjugated Fatty Acid Methyul Esters by Silver Ion-High-Performance Liquid Chromatography", Lipids, 34(4):407-412.
Selin CLA Product Literature Jan. 1997.
Shanta et al., 1993, "Conjugated Linoleic Acid Concentrations in Processed Cheese Containing Hydrogen Donors, Iron and Dairy-Based Additives", Food Chemistry, 47:257-261.
Shantha et al., 1995, J. Food Sci, 60:695.
Sugano et al., 1998, "Conjugated Linoleic Acid Modulates Tissue Levels of Chemical Mediators and Immunoglubulins in Rats", Lipids 33(5):521-27.

Theil et al., 1998, "Conjugated Linoleic Acid Improves Performance and Body Composition in Swine", Iowa State University, Midwest Animal Sciences Meeting, Abstract 127:61.

Yurawecz et al., 1999, Lipid, 8:277-282.

Zambell et al., 2000, Lipids, 35:777-782.

Bhaggan; Declaration (Jun. 24, 2009); in re the opposition to European Patent No. 0950410; Application Serial No. 99105497.4; Applicant: Aker Biomarine ASA; pp. 1-7.

Sassano; Declaration (Jul. 1, 2009); in re the opposition to European Patent No. 0950410; Application Serial No. 99105497.4; Applicant: Aker Biomarine ASA; pp. 1-7.

Decision of the Opposition Division; in re EP Patent Application Serial No. 99105497.4-2112 Patnet No. 950410; Applicant: Aker Biomarkine ASA; Dated Dec. 22, 2009; pp. 1-29.

Japan Oil Chemists' Society, "Oil Chemistry Handbook—lipid and surface-active agent—", Maruzen K.K., Nov. 20, 2011, fourth edition, p. 510.

Mieko Iwai, "Lipase—its basic and application," Sachi Shobo K.K., Jul. 25, 1991, first edition, first copy, p. 286-287.

* cited by examiner

Fig. 1.: OSI (Oxygen Stability Index) values of CLA TG stored at 60°C with four different antioxidants

CONJUGATED LINOLEIC ACID COMPOSITIONS

RELATED APPLICATIONS

The application is a continuation of U.S. Ser. No. 09/544,084, filed Apr. 6, 2000, which is a continuation-in-part of U.S. Ser. No. 09/132,593, filed Aug. 11, 1998 and U.S. Ser. No. 09/270,940, filed Mar. 17, 1999, which is a continuation-in-part of U.S. Ser. No. 09/042,767, filed Mar. 17, 1998, now U.S. Pat. No. 6,015,833, and U.S. Ser. No. 09/042,538, filed Mar. 17, 1998.

FIELD OF THE INVENTION

The present invention relates to the field of human and animal nutrition, and in particular to certain novel compositions of conjugated linoleic acids (CLA). These compositions are prepared according to a novel method that controls oxidation of CLA into volatile organic compounds and in some cases contain antioxidants that control oxidation.

BACKGROUND OF THE INVENTION

In 1978, researchers at the University of Wisconsin discovered the identity of a substance contained in cooked beef that appeared to inhibit mutagenesis. The substance was found to be a mixture of positional isomers of linoleic acid (C18:2) having conjugated double bonds. The c9,t11 and t10,c12 isomers are present in greatest abundance, but it is uncertain which isomers are responsible for the biological activity observed. It has been noted from labelled uptake studies that the 9,11 isomer appears to be somewhat preferentially taken up and incorporated into the phospholipid fraction of animal tissues, and to a lesser extent the 10,12 isomer. (Ha, et al., *Cancer Res.*, 50: 1097 [1990]).

The biological activity associated with conjugated linoleic acids (termed CLA) is diverse and complex. At present, very little is known about the mechanisms of action, although several preclinical and clinical studies in progress are likely to shed new light on the physiological and biochemical modes of action. The anticarcinogenic properties of CLA have been well documented. Administration of CLA inhibits rat mammary tumorigenesis, as demonstrated by Birt, et al., *Cancer Res.*, 52: 2035s [1992]. Ha, et al., *Cancer Res.*, 50: 1097 [1990] reported similar results in a mouse forestomach neoplasia model. CLA has also been identified as a strong cytotoxic agent against target human melanoma, colorectal and breast cancer cells in vitro. A recent major review article confirms the conclusions drawn from individual studies (Ip, Am. J. Clin. Nutr., 66 (6 Supp): 1523s [1997]).

Although the mechanisms of CLA action are still obscure, there is evidence that some component(s) of the immune system may be involved, at least in vivo. U.S. Pat. No. 5,585,400 (Cook, et al., incorporated herein by reference), discloses a method for attenuating allergic reactions in animals mediated by type I or TgE hypersensitivity by administering a diet containing CLA. CLA in concentrations of about 0.1 to 1.0 percent was also shown to be an effective adjuvant in preserving white blood cells. U.S. Pat. No. 5,674,901 (Cook, et al.), incorporated herein by reference, disclosed that oral or parenteral administration of CLA in either free acid or salt form resulted in elevation in CD-4 and CD-8 lymphocyte subpopulations associated with cell-mediated immunity. Adverse effects arising from pretreatment with exogenous tumor necrosis factor could be alleviated indirectly by elevation or maintenance of levels of CD-4 and CD-8 cells in animals to which CLA was administered. Finally, U.S. Pat. No. 5,430,066, incorporated herein by reference, describes the effect of CLA in preventing weight loss and anorexia by immune stimulation.

Apart from potential therapeutic and pharmacologic applications of CLA as set forth above, there has been much excitement regarding the use of CLA nutritively as a dietary supplement. CLA has been found to exert a profound generalized effect on body composition, in particular redirecting the partitioning of fat and lean tissue mass. U.S. Pat. No. 5,554,646 (Cook, et al.), incorporated herein by reference, discloses a method utilizing CLA as a dietary supplement in which pigs, mice, and humans were fed diets containing 0.5 percent CLA. In each species, a significant drop in fat content was observed with a concomitant increase in protein mass. It is interesting that in these animals, increasing the fatty acid content of the diet by addition of CLA resulted in no increase in body weight, but was associated with a redistribution of fat and lean within the body. Another dietary phenomenon of interest is the effect of CLA supplementation on feed conversion. U.S. Pat. No. 5,428,072 (Cook, et al, incorporated herein by reference), provided data showing that incorporation of CLA into animal feed (birds and mammals) increased the efficiency of feed conversion leading to greater weight gain in the CLA supplemented animals. The potential beneficial effects of CLA supplementation for food animal growers is apparent.

Another important source of interest in CLA, and one which underscores its early commercial potential, is that it is naturally occurring in foods and feeds consumed by humans and animals alike. In particular, CLA is abundant in products from ruminants. For example, several studies have been conducted in which CLA has been surveyed in various dairy products. Aneja, et al., *J. Dairy Sci.*, 43: 231 [1990] observed that processing of milk into yogurt resulted in a concentration of CLA. (Shanta, et al., *Food Chem.*, 47: 257 [1993]) showed that a combined increase in processing temperature and addition of whey increased CLA concentration during preparation of processed cheese. In a separate study, Shanta, et al., *J. Food Sci.*, 60: 695 [1995] reported that while processing and storage conditions did not appreciably reduce CLA concentrations, they did not observe any increases. In fact, several studies have indicated that seasonal or interanimal variation can account for as much as three fold differences in CLA content of cows milk. (See e.g., Parodi, et al., *J. Dairy Sci.*, 60: 1550 [1977]). Also, dietary factors have been implicated in CLA content variation, as noted by Chin, et al., *J. Food Camp. Anal.*, 5: 185 [1992]. Because of this variation in CLA content in natural sources, ingestion of prescribed amounts of various foods will not guarantee that the individual or animal will receive the optimum doses to ensure achieving the desired nutritive effect.

Linoleic acid is an important component of biolipids, and comprises a significant proportion of triglycerides and phospholipids. Linoleic acid is known as an "essential" fatty acid, meaning that the animal must obtain it from exogenous dietary sources since it cannot be autosynthesized. Incorporation of the CLA form of linoleic acid may result in a direct substitution of CLA into lipid positions where unconjugated linoleic would have migrated. However, this has not been proven, and some of the highly beneficial but unexplained effects observed may even result from a repositioning of CLA within the lipid architecture at sites where unconjugated linoleic acid would not have otherwise migrated. It is now clear that one source of animal CLA, especially in dairy products, comes from the biochemical action of certain rumen bacteria on native linoleic acid, first isomerizing the linoleic acid to CLA, and then secreting it into the rumen cavity. Kepler, et al., *J. Nutrition,* 56: 1191 [1966] isolated a rumen bacterium, *Butyrivibrio ibrisolvens*, which catalyzes formation of 9,11-CLA as an intermediate in the biohydrogenation of linoleic acid. Chin, et al., *J. Nutrition,* 124: 694 [1994] further found that CLA found in the tissues of rodent was associated with bacteria, since corresponding germ-free rats produced no CLA.

In the development of a defined commercial source of CLA for both therapeutic and nutritional application, a process for generating large amounts of defined material is needed. The problem with most CLA products made by conventional approaches is their heterogeneity, and substantial variation in isoform from batch to batch. Considerable attention has been given to the fact that the ingestion of large amounts of hydrogenated oils and shortenings, instead of animal tallow, has resulted in a diet high in trans-fatty acid content. For example, Holman, et al., *PNAS,* 88:4830 [1991] showed that rats fed hydrogenated oils gave rise to an accumulation in rat liver of unusual polyunsaturated fatty acid isomers, which appeared to interfere with the normal metabolism of naturally occurring polyunsaturated fatty acids. These concerns were summarized in an early Editorial in *Am. J. Public Health,* 84: 722 (1974). Therefore, there exists a strong need for a biologically active CLA product of defined composition.

SUMMARY OF THE INVENTION

Figure 1:
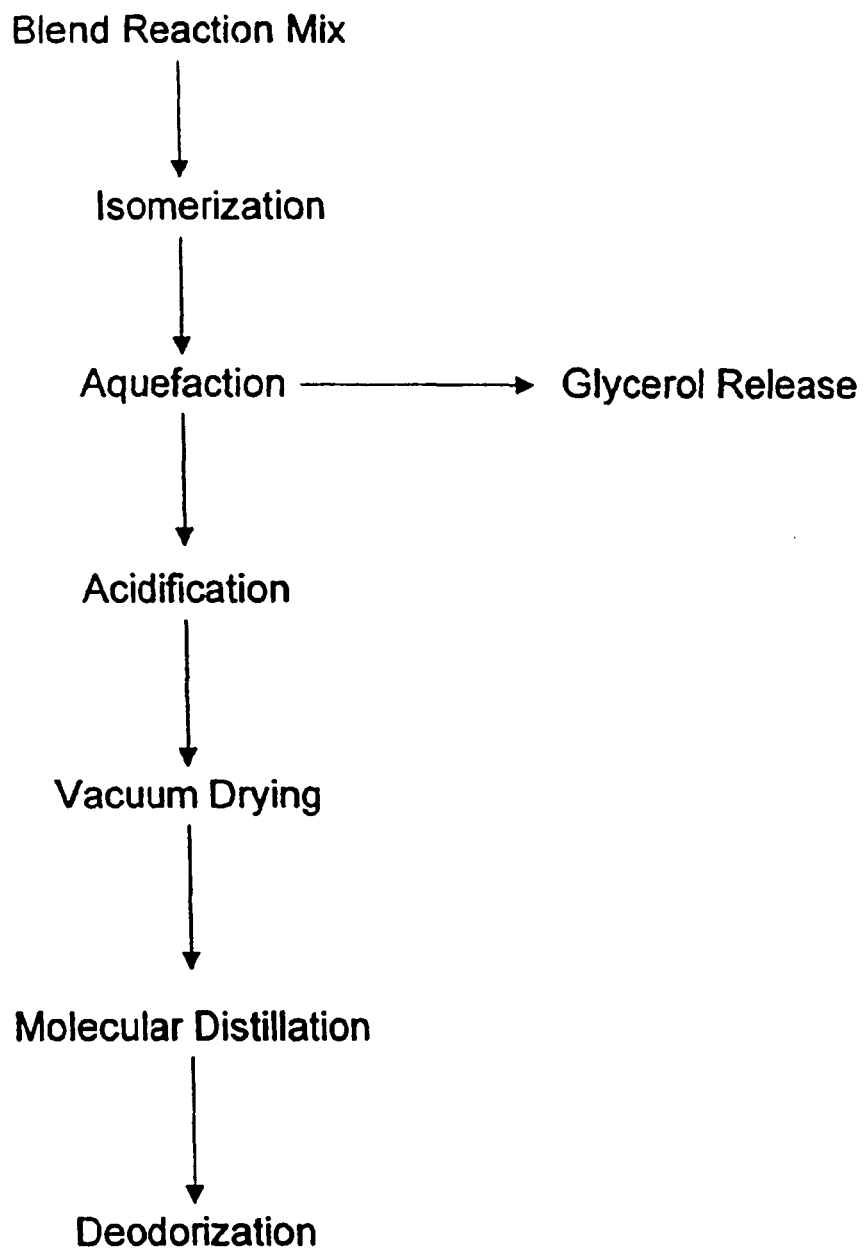
FIG. 1 is a flow diagram of the alkali isomerization process of the present invention.

The present invention relates to the field of human and animal nutrition, and in particular to certain novel compositions of conjugated linoleic acids (CLA). These compositions are prepared according to a novel method that controls oxidation of CLA into volatile organic compounds and in some embodiments contain antioxidants that control oxidation.

The present invention provides a composition comprising an isomerized (i.e., conjugated) linoleic acid moiety of high purity. The CLA moiety is not limited to any one specific CLA moiety. Several different moieties are contemplated by the present invention. In some embodiments, the CLA moiety is a free fatty acid. In other embodiments, the CLA moiety is an alkyl ester. In still further embodiments, the CLA moiety is a triacylglyceride.

In some embodiments of the present invention, the composition further comprise a metal oxidant chelator. The present invention is not limited to any one metal oxidant chelator. A variety of metal oxidant chelators are contemplated by the present invention. In some embodiments, the metal oxidant chelator comprises citric acid esters. In other embodiments, the metal oxidant chelator comprises lecithin.

The purity of the isomerized linoleic acid composition is not limited to any specific level. Several levels of purity are contemplated by the present invention. In some embodiments, the composition contains less than 100 parts per million total of volatile organic compounds. In other embodiments, the composition contains less than 50 parts per million total of volatile organic compounds. In still other embodiments, the composition contains less than 10 parts per million total of volatile organic compounds. In still further embodiments, the composition contains less than 5 parts per million total of volatile organic compounds.

In some embodiments, the present invention provides a food product comprising a isomerized conjugated linoleic acid moiety of high purity and an metal oxidant chelator. The purity of the food product containing an isomerized linoleic acid composition is not limited to any specific level. Several levels of purity are contemplated by the present invention. In some embodiments, the composition contains less than 100 parts per million total of volatile organic compounds. In other embodiments, the composition contains less than 50 parts per million total of volatile organic compounds. In still other embodiments, the composition contains less than 10 parts per million total of volatile organic compounds. In further embodiments, the composition contains less than 5 parts per million total of volatile organic compounds.

The CLA moiety contained in the food product of present invention is not limited to any one specific CLA moiety. Several different CLA moieties are contemplated by the present invention. In some embodiments, the CLA moiety is a free fatty acid. In other embodiments, the CLA moiety is an alkyl ester. In still further embodiments, the CLA moiety is a triacylglyceride.

The present invention is not limited to any one metal oxidant chelator. A variety of metal oxidant chelators are contemplated by the present invention. In some embodiments, the metal oxidant chelator comprises citric acid esters. In other embodiments, the metal oxidant chelator comprises lecithin.

In some embodiments, the present invention provides a food supplement comprising a isomerized conjugated linoleic acid moiety of high purity and an metal oxidant chelator. The purity of the food product containing an isomerized linoleic acid composition is not limited to any specific level. Several levels of purity are contemplated by the present invention. In some embodiments, the composition contains less than 100 parts per million total of volatile organic compounds. In other embodiments, the composition contains less than 50 parts per million total of volatile organic compounds. In still other embodiments, the composition contains less than 10 parts per million total of volatile organic compounds. In further embodiments, the composition contains less than 5 parts per million total of volatile organic compounds.

The CLA moiety contained in the food supplement of present invention is not limited to any one specific CLA moiety. Several different CLA moieties are contemplated by the present invention. In some embodiments, the CLA moiety is a free fatty acid. In other embodiments, the moiety is an alkyl ester. In further embodiments, the CLA moiety is a triacylglyceride.

The present invention is not limited to any one metal oxidant chelator. A variety of metal oxidant chelators are contemplated by the present invention. In some embodiments, the metal oxidant chelator comprises citric acid esters. In other embodiments, the metal oxidant chelator comprises lecithin.

In some embodiments, the present invention provides a method comprising providing a linoleic acid containing seed oil; isomerizing the linoleic acid to form conjugated linoleic acids; and treating the conjugated linoleic acids to obtain a CLA composition of high purity.

Several levels of purity are contemplated by the method of the present invention. In some embodiments, the composition less than 100 parts per million total of volatile organic compounds. In some embodiments, the CLA composition contains less than 50 parts per million total of volatile organic compounds. In other embodiments, the CLA composition contains less than 10 parts per million total of volatile organic compounds. In further embodiments, the CLA composition contains less than 5 parts per million total of volatile organic compounds.

In other embodiments of the present invention, a composition is provided comprising a CLA moiety having a sufficiently low volatile organic compound concentration so that the taste and smell of said composition is not affected. In still further embodiments of the present invention, a food product is provided that comprises a conjugated linoleic acid moiety having a sufficiently low volatile organic compound concentration so that the taste and smell of the food product is not affected.

DEFINITIONS

As used herein, "conjugated linoleic acid" or "CLA" refers to any conjugated linoleic acid or octadecadienoic free fatty acid. It is intended that this term encompass and indicate all positional and geometric isomers of linoleic acid with two conjugated carbon-carbon double bonds any place in the molecule. CLA differs from ordinary linoleic acid in that ordinary linoleic acid has double bonds at carbon atoms 9 and 12. Examples of CLA include cis- and trans isomers ("E/Z isomers") of the following positional isomers: 2,4-octadecadienoic acid, 4,6-octadecadienoic acid, 6,8-octadecadienoic acid, 7,9-octadecadienoic acid, 8,10-octadecadienoic acid, 9,11-octadecadienoic acid and 10,12 octadecadienoic acid, 11,13 octadecadienoic acid. As used herein, "CLA" encompasses a single isomer, a selected mixture of two or more isomers, and a non-selected mixture of isomers obtained from natural sources, as well as synthetic and semisynthetic CLA.

As used herein, the term "isomerized conjugated linoleic acid" refers to CLA synthesized by chemical methods (e.g., aqueuous alkali isomerization, non-aqueous alkali isomerization, or alkali alcoholate isomerization).

As used herein, the term "conjugated linoleic acid moiety" refers to any compound or plurality of compounds containing conjugated linoleic acids or derivatives. Examples include, but are not limited to fatty acids, alkyl esters, and triglycerides of conjugated linoleic acid.

As used herein, it is intended that "triglycerides" of CLA contain CLA at any or all of three positions (e.g., SN-1, SN-2, or SN-3 positions) on the triglyceride backbone. Accordingly, a triglyceride containing CLA may contain any of the positional and geometric isomers of CLA.

As used herein, it is intended that "esters" of CLA include any and all positional and geometric isomers of CLA bound through an ester linkage to an alcohol or any other chemical group, including, but not limited to physiologically acceptable, naturally occurring alcohols (e.g., methanol, ethanol, propanol). Therefore, an ester of CLA or esterified CLA may contain any of the positional and geometric isomers of CLA.

It is intended that "non-naturally occurring isomers" of CLA include, but are not limited to c11,t13; t11,c13; t11,t13; c11,c13; c8,t10; t8,c10; t8,t10; c8,c10; and trans-trans isomers of octadecadienoic acid, and does not include t10,c12 and c9,t11 isomers of octadecadienoic acid. "Non-naturally occurring isomers" may also be referred to as "minor isomers" of CLA as these isomers are generally produced in low amounts when CLA is synthesized by alkali isomerization.

As used herein, "low impurity" CLA refers to CLA compositions, including free fatty acids, alkylesters, and triglycerides, which contain less than 1% total 8,10 octadecadienoic acids, 11,13 octadecadienoic acids, and trans-trans octadecadienoic acids.

As used herein, "c" encompasses a chemical bond in the cis orientation, and "t" refers to a chemical bond in the trans orientation. If a positional isomer of CLA is designated without a "c" or a "t", then that designation includes all four possible isomers. For example, 10,12 octadecadienoic acid encompasses c10,t12; t10,c12; t10,t12; and c10,c12 octadecadienoic acid, while t10,c12 octadecadienoic acid or CLA refers to just the single isomer.

As used herein, the term "oil" refers to a free flowing liquid containing long chain fatty acids (e.g., CLA), triglycerides, or other long chain hydrocarbon groups. The long chain fatty acids, include, but are not limited to the various isomers of CLA.

As used herein, the term "physiologically acceptable carrier" refers to any carrier or excipient commonly used with oily pharmaceuticals. Such carriers or excipients include, but are not limited to, oils, starch, sucrose and lactose.

As used herein, the term "oral delivery vehicle" refers to any means of delivering a pharmaceutical orally, including, but not limited to, capsules, pills, tablets and syrups.

As used herein, the term "food product" refers to any food or feed suitable for consumption by humans, non-ruminant animals, or ruminant animals. The "food product" may be a prepared and packaged food (e.g., mayonnaise, salad dressing, bread, or cheese food) or an animal feed (e.g., extruded and pelleted animal feed or coarse mixed feed). "Prepared food product" means any pre-packaged food approved for human consumption.

As used herein, the term "foodstuff" refers to any substance fit for human or animal consumption.

As used herein, the term "volatile organic compound" refers to any carbon-containing compound which exists partially or completely in a gaseous state at a given temperature. Volatile organic compounds may be formed from the oxidation of an organic compound (e.g., CLA). Volatile organic compounds include, but are not limited to pentane, hexane, heptane, 2-butenal, ethanol, 3-methyl butanal, 4-methyl pentanone, hexanal, heptanal, 2-pentyl furan, octanal.

As used herein, the term "metal oxidant chelator" refers to any antioxidant that chelates metals. Examples include, but are not limited to lecithin and citric acid esters.

As used herein, the term "alcoholate catalyst" refers to alkali metal compounds of any monohydric alcohol, including, but not limited to, potassium methylate and potassium ethylate.

DETAILED DESCRIPTION OF THE INVENTION

The compositions of the present invention result from a highly controlled isomerization process, and from using the preferred starting materials of sunflower, safflower, or corn oil. This composition has not heretofore been obtained, for application to an industrial scale, because the conventional processes historically produce conjugated linoleic acids for entirely different purposes, namely, as drying oils in the paint industry. Also, there has not been an appreciation of the implications of the isomer content of the final product, because the analytical methods for characterizing the fatty acids has not been widely available. Furthermore, the present invention provides a method for preventing oxidation of CLA during storage to form volatile organic compounds.

I. Methods for Conjugating Linoleic Acids

In the older isomerization processes, some of which are still in use in more modern format, production of the conjugated fatty acids was carried out in aqueous alkali (generally NaOH) at high temperatures in excess of 200° C. and usually at superatmospheric pressures. For example, U.S. Pat. No. 2,350,583 (Bradley) discloses an aqueous alkali process utilizing treated soaps in which both conjugation and polymerization occurred under rather harsh conditions at 200 to 250° C. for a period of several hours. The fractions of drying oil, starting with linseed oil, were obtained by distillation (see also Br. Pat. No. 558,881 for a very similar process). In a variation of the process, U.S. Pat. No. 4,381,264 teaches a process where a low water content reaction zone (0.5% water) contains stoichiometric base in the presence of $SO_2$ to obtain conjugation of the double bonds of various polyunsaturated fatty acids. The aqueous alkali process was adapted in U.S. Pat. No. 4,164,505 to a continuous flow process in which an alkali metal hydroxide and water are continuously charged in a flow zone maintained at between 200 and 370° C. At these temperatures, the time of reaction should be greatly foreshortened, but there is relatively little control over the isomerization. At the higher end of the temperature range, one skilled in the art would predict almost complete conversion to double trans species.

Methods of producing CLA using various nonaqueous solvents and catalysts have been described in the literature. Burr (U.S. Pat. No. 2,242,230) discloses the use of solvents such as methanol, butanol, ethanol and glycol in combination with various catalysts. These reaction parameters are summarized in Table 1. With the exception of glycol, the reactions were conducted either under reflux conditions or in sealed tubes. These reaction conditions result in imprecise control of two of the important reactions parameters—temperature and pressure. Imprecise control of these reactions parameters is likely to lead to less than complete conjugation and the formation of undesirable isomers.

TABLE 1

Patent 2,242,230

| Solvent | Catalyst | Temperature | Time |
|---|---|---|---|
| Ethanol | KOH, NaOH | reflux or higher* | varied |
| Butanol | KOH, NaOH | reflux or higher* | varied |
| Glycol | KOH | 195° C. | varied |
| Isoamyl Alcohol | KOH | reflux or higher* | varied |
| Butanol | Tributyl-amine | 140-175° C. | 22 hours |
| Butanol | Potassium Acetate | 175° C. | 36 hours |
| Butanol | Trisodium Phosphate | 175° C. | 36 hours |
| Butanol | Potassium Phosphate | 175° C. | 36 hours |
| Butanol | Sodium Benzoate | 175° C. | 36 hours |
| Butanol | Potassium Thiocyanate | 175° C. | 36 hours |
| Butanol | Borax | 175° C. | 36 hours |

Likewise, Baltes et al., (U.S. Pat. No. 3,162,658) disclose the use of nonaqueous solvents and various metallic bases as catalysts for the conjugation of fatty acids. The various reaction parameters of the methods described by Baltes et al. are summarized in Table 2. Baltes et al. also disclose the use various low boiling point solvents. As most of these reactions were conducted at temperatures above the boiling point of the solvent employed, it is apparent that the reactions were conducted under pressure, which is an independent factor influencing the formation of octadecadienoic acid isomers. The product derived from these reactions will thus contain undesirable isomers.

TABLE 2

Patent 3,162,658

| Solvent | Catalyst | Temperature | Time |
|---|---|---|---|
| Methanol | KOH | 60-140° C. | variable |
| Methanol | Potassium Methylate | 140° C. | variable |
| Butanol | Potassium Methylate | 140° C. | variable |
| Ethanol | Potassium Methylate | 140° C. | variable |
| Isopropanol | Potassium Methylate | 120-140° C. | variable |
| Heptane/3° Butanol | Potassium Butylate | reflux | variable |
| 3° Butanol | Cesium Butylate | 140° C. | variable |
| Ethylene Diamine | Potassium Methylate | 140-160° C. | variable |
| Methanol | Sodium Amide | 140° C. | variable |

II. Controlled Isomerization Reactions

The CLA of the present invention lacks significant amounts of isomers such as the 8,10 isomer, the 11,13 isomer, and the various trans-trans isomers. These compositions were produced by a tightly controlled nonaqueous alkali isomerization process presented in flow diagram form in FIG. 1 and by isomerization with alkali alcoholate catalysts. In some embodiments, sunflower oil, safflower oil, or corn oil are reacted at an ambient pressure under an inert gas atmosphere with an excess of alkali in a high-boiling point solvent, namely propylene glycol at a temperature below the boiling point of the solvent. In other embodiments, sunflower oil, safflower oil, or corn oil are reacted in the presence of an alkali alcoholate catalyst and a small amount of a suitable solvent.

A. Sources of Linoleic Acid

The preferred oils for conjugation are sunflower, safflower oil, and corn oil. As compared to soybean oil, these oils have lower concentrations of undesirable components such as phosphatides and sterols. These undesirable components may contribute to the formation of gums which foul the conjugation equipment and other undesirable polymers. Various properties of these oils are summarized in Tables 3, 4, and 5.

COMPARISON OF CONTAMINANTS

TABLE 3

| Phosphatides | |
|---|---|
| Soybean | 1.5-3.0% |
| Sunflower | .4-1% |
| Sunflower | .4-1% |

TABLE 4

Sterols (unsaponifiables by percent*)

| Soybean | | Sunflower | | Safflower | |
|---|---|---|---|---|---|
| Campesterol | 20* | Campesterol | 8 | Campesterol | 13 |
| Stigmasterol | 20 | Stigmasterol | 8 | Stigmasterol | 9 |
| β-Sitosterol | 53 | β-Sitosterol | 60 | β-Sitosterol | 52 |
| $\Delta^5$ Avensterol | 3 | $\Delta^5$ Avensterol | 4 | $\Delta^5$ Avensterol | 1 |
| $\Delta^7$ Stigmasterol | 3 | $\Delta^7$ Stigmasterol | 15 | $\Delta^7$ Stigmasterol | 15 |
| $\Delta^7$ Avenasterol | 1 | Avenasterol | 4 | Avenasterol | 3 |
| 0.36% total in oil | | 0.36% total in oil | | 0.36% total in oil | |

*May not equal 100

TABLE 5

|  | Soybean | Sunflower | Safflower |
|---|---|---|---|
| Iodine Value | 134.6 | 135.4 | 143.6 |
| Saponification value | 190.7 | 190.6 | 190.3 |
| Unsaponification value | .6 | .7 | .6 |

B. Isomerization with Propylene Glycol as a Solvent

In some embodiments of the present invention, the conjugated linoleic acid is produced by nonaqueous alkali isomerization. The reaction conditions of the controlled isomerization process allow for precise control of the temperature (and constant ambient pressure) of the conjugation process. Preferably the alkali is an inorganic alkali such as potassium hydroxide, cesium hydroxide, cesium carbonate or an organic alkali such as tetraethyl ammonium hydroxide. The catalyst is preferably provided in a molar excess as compared to the fatty acid content of oil. The solvent is propylene glycol. Preferably, the reaction is conducted within a temperature range 130 to 165° C., most preferably at about 150° C. The time of the reaction may vary, however, there is an increased likelihood of the formation of undesirable isomers when the reaction is conducted for long periods of time. A relatively short reaction time of 2.0 to 6.5 hours has proved satisfactory for excellent yields.

It will be understood to a person skilled in the art that to produce the desired composition, the reaction conditions described above may be varied depending upon the oil to be conjugated, the source of alkali, and equipment. Preanalysis of a particular oil may indicate that the conditions must be varied to obtain the desired composition. Therefore, the temperature range, pressure, and other reaction parameters represent a starting point for design of the individual process and are intended as a guide only. For example, it is not implied that the described temperature range is the only range which may be used. The essential aspect is to provide precise temperature control. However, care must be taken because increasing the pressure may lead to less than complete isomerization and the formation of undesirable isomers. Finally, the length of the conjugation reaction may be varied. Generally, increasing amounts of undesirable isomers are formed with increasing length or reaction time. Therefore, the optimal reaction time allows the reaction to go nearly or essentially to completion but does not result in the formation of undesirable isomers.

Following the conjugation reaction, the resulting CLA containing composition may be further purified according to FIG. 1. To separate the fatty acids from the conjugation reaction mix, the reaction mix is cooled to approximately 95° C., an excess of water at 50° C. is added, and the mixture slowly stirred while the temperature is reduced to about 50° C. to 60° C. Upon addition of the water, a soap of the fatty acids is formed and glycerol is formed as a by-product. Next, a molar excess of concentrated HCl is added while stirring. The aqueous and nonaqueous layers are then allowed to separate at about 80-90° C. The bottom layer containing water and propylene glycol is then drawn off. The remaining propylene glycol is removed by vacuum dehydration at 60-80° C.

The dried CLA composition may then preferably be degassed in degassing unit with a cold trap to remove any residual propylene glycol. Next, the CLA is distilled at 190° C. in a molecular distillation plant at a vacuum of $10^{-1}$ to $10^{-2}$ millibar. The advantage of this purification system is the short time (less than one minute) at which the CLA is held at an elevated temperature. Conventional batch distillation procedures are to be strictly avoided since they involve an elevated temperature of approximately 180-200° C. for up to several hours. At these elevated temperatures the formation of undesirable trans-trans isomers will occur. Approximately 90% of the feed material is recovered as a slightly yellow distillate. The CLA may then be deodorized by heating to about 120°-170° C., preferably at about 150° C. for 2 hours to improve smell and taste. Excessive heat may result in the formation of trans-trans isomers. These procedures produce a CLA composition with a solvent level of less than about 5 ppm, preferably less than about 1 ppm. This process eliminates toxic trace levels of solvent so that the resulting composition is essentially free of toxic solvent residues.

The processes described above are readily adaptable to both pilot and commercial scales. For example, 400 kg of safflower oil may be conjugated at 150° C. for 5 hours in 400 kg of propylene glycol with 200 kg KOH added as a catalyst. The resulting CLA may then be purified as described above. Further, commercial scale batch systems may be easily modified to produce the desired CLA composition. For example, stainless steel reactors should be preferably glass lined to prevent corrosion due to pH levels of below 3.0. However, it should be noted that conjugation processes utilizing nonaqueous solvents are generally less corrosive than those conducted with water.

Several comparative experiments were carried out to highlight the key properties of the present CLA compositions in contrast to those made under either suboptimal conditions or in accordance with the aqueous alkali methods of the prior art. In Example 1, the CLA was prepared by the present method. CLA was produced by the conventional aqueous alkali method in Example 2. In Example 3, the reaction of Example 1 is substantially repeated, only at high temperature. Finally, in Example 4, the aqueous alkali reaction substantially identical to that of Example 2 is run at low temperature. The precise conditions and details of each experiments are set forth in the Examples. The profiles of the analysis of the CLA isomer content are set forth in Tables 6-11.

Referring to the data in Table 6, the relative area percentage is given for each identified peak corresponding to the individual isomers, for each of the four experiments. The GC plot gave a number of peaks for each sample tested. The area under each of these peaks was integrated to obtain a total value. The identity of the peak was determined by its relative position, from published atlases of standard elution profiles, and the scientific literature. The top row represents the residual value for unconjugated starting material, 9,12-linoleic acid. Both low and high temperature reaction in propylene glycol gave extremely high conversions of over 99 percent of the total starting material.

Referring to column 1, it is apparent that unlike any of the control compositions, in Example 1, a peak corresponding to 11,13 mixture of isomers, the peak corresponding to c11,c13 specifically, the peaks for any of the 8,10 isomers, and the peak for unidentified isomers are all entirely missing. In the case of c9,t11 isomer, the peaks in GC for both the 8,10 and 9,11 isomers are superimposed, and are here resolved only for Example 1 material by subtracting out that portion of the peak identified as 8,10 by NMR studies. This was not done in the other experiments, so that row 3 gives the values for combined 8,10 and 9,11 for Examples 2-4. In general, for the 8,10, 11,13, and unidentified isomers, a value of less than 1 percent down to undetectable is of therapeutic and nutritional value, because it reduces to trace levels potentially deleterious contaminants, especially those known to have suspect absorption pathways in lipogenesis. In non-ruminants, for example, addition of 0.25 to 2.5 percent CLA to the diet can increase the incidence of CLA in tissues to approximate that in ruminants, so that other animals can be a source of CLA provided adulterating isomers are not present.

Example 2 provides a typical aqueous alkali product representative of conventionally manufactured CLAs. Conversion is less efficient both overall, and in producing the c9,t11 and t10,c12 isomers. Note also a high percentage of the suspect 11,13 isomers, and a significant percentage of unidentified material.

Example 3 illustrates the criticality of the temperature parameter. An upward shift in temperature in propylene glycol media sharply increases the amount of the contaminating isomers at the expense of the c9,t11 and t10,c12 isomers. Also of interest, at the higher temperature there is a dramatic increase in the trans, trans species, as double bond rearrangements are favored which yield a more stable electron configuration at levels of increased energy stress.

Example 4 illustrates that decreasing the temperature in the aqueous alkali system, in fact, reduces the amounts of some of the contaminating isomers. However, there is a dramatic drop in yield, and the level of the 11,13 group of isomers remains very high, suggesting that the formation of this electron configuration is influenced more by the action of base in an aqueous medium, than is explained by overall kinetic energy in the system. Note also the extremely long reaction time of 22.5 hours; too long for an efficient industrial scale batch process.

Table 6 converts the relative isomer percentages in the various reactions as a function of peak area to their corresponding peak ratios. The present process produces a virtually complete conversion of 9,12-linoleic acid to an approximate equal amount of each of the two desired CLA isomers. At the higher temperature, even in propylene glycol, the incidence of the 11,13 isomer is still less one third that of the low temperature aqueous alkali process.

C. Isomerization with Alcoholate Catalysts

In some embodiments, the present invention also provides methods for producing alkyl esters of CLA. After fat splitting and dehydration, the free fatty acids are combined with methanol or another monohydric low molecular weight alcohol and heated to the temperature at which the alcohol boils. Esterification proceeds under refluxing conditions with removal of the reaction water through a condenser. After the addition of a further quantity of the same or a different monohydric alcohol an alcoholate catalyst is blended into the ester mix (See, e.g., U.S. Pat. No. 3,162,658, incorporated herein by reference). Typical alcoholate catalysts are sodium or potassium ethoxide, or their methyl, butyl, or propyl counterparts.

In the esterification, methanol or ethanol are preferred, although other branched or straight chain monohydric alcohols may be used. The longer the aliphatic chain of the alkyl group, the more lipid compatible the material becomes. Also the viscosity tends to increase. For different types of feed or food, whose consistency varies, product of varying viscosity can be used to obtain the desired flow or compounding characteristics without affecting the therapeutic or nutritional properties arising from the CLA moieties. The theory and practice of esterification are conventional. A basic explanation of the most common methods is set forth in the McGraw-Hill Encyclopedia of Science & Technology, McGraw-Hill Book Co., N.Y.: 1996 (5th ed.). The animal and human body has a variety of esterases, so that the CLA-ester is cleaved to release the free fatty acids readily. Tissue uptake may have a different kinetics depending on the tissue involved and the benefit sought.

In the isomerization step, it was found that alcoholate catalysis produced a much superior product than aqueous alkali mediated isomerization. The latter process always produced undesirable isomers even under mild reaction conditions. The milder conditions do give lower amounts of unwanted isomers, but at the great expense of yield, as shown in the Examples. In most systems the appearance of the c9,t11 and t10,c12 isomers dominates and they are formed in roughly equimolar amounts. It has not heretofore been possible to control the isomerization of the one isomer to the exclusion of the other. While it is desirable to increase the percentage of one or the other isomer (depending on the physiological effect to be achieved), at present this must largely be carried out by adding an enriched source of the desired isomer.

The preferred starting materials for conjugation with alcoholate catalysts are sunflower oil, safflower oil, and corn oil. Each of these oils contains high levels of linoleic acid and low levels of linolenic acid. As shown in Example 18, conjugation of linolenic acid results in the formation of several uncharacterized fatty acid moieties, the biological properties of which are unknown. Previous conjugation processes were not concerned with the production of unknown compounds because the products were used in drying oils, paints and varnishes and not in products destined from human or animal consumption. Accordingly, the CLA produced by those processes with oils containing high levels of linolenic acid were not suitable for nutritional uses.

In some embodiments, it is further contemplated that glycerol and esters of glycerol should be removed before making monoesters of fatty acids. Traces of glycerol present during conjugation contribute to the production of trimethoxypropane and triethoxypropane. Therefore, prior to conjugation, it is preferable to distill monoesters obtained by alcoholysis.

D. Triacylglyceride Derivatives of CLA

The present invention contemplates the use of derivatives of CLA. For example, CLA may be free or bound through ester linkages as described above or provided in the form of an oil containing CLA triglycerides, as described in Examples 5, 6, and 14. In these embodiments, the triglycerides may be partially or wholly comprised of CLA attached to a glycerol backbone. The CLA may also preferably be provided as a methylester or ethylester as described in Examples 8 and 9. Furthermore, the CLA may be in the form of a non-toxic salt, such as a potassium or sodium salt (e.g., a salt formed by reacting chemically equivalent amounts of the free acids with an alkali hydroxide at a pH of about 8 to 9).

In one embodiment of the present invention, a novel triacylglycerol is synthesized comprising the novel CLA isomer mixture disclosed hereinafter for non-aqueous isomerization of linoleic acid from sunflower and/or safflower oils. The pure triacylglycerols highly enriched for CLA (90-96 percent) may be confirmed by H NMR. Esterification proceeds using immobilized *Candida antarctica* Lipase. Preferably, the CLA will contain at least 40 and upwardly 45-48 percent of c9,t11-octadecadienoic and t10,c12-octadecadienoic acids, and mixtures thereof. There will be less than one percent esters 8,10; 11,13; and trans, trans isomers or less than five percent in the aggregate. In some embodiments, the resultant triacylglycerol is not purified further to remove all levels of phosphatidyl and sterol residues. But those levels remaining from isomerization of sunflower and safflower oils will be adequate for commercial applications involving safe, edible products in feed and food. In other embodiments, the triacylglycerol is further purified by molecular distillation.

The immobilized *Candida antarctica* lipase is to be employed in a manner similar to that described for n-3 type polyunsaturated fatty acids, in Harraldson et al. The esterification reaction is conducted at 50°-75° C., preferably 65° C., in the absence of any solvent and a vacuum employed in order to remove the co-produced water or alcohols (from esters) upon formation. This shifts the triacylglycerol production to completion and ensures a highly pure product virtually free of any mono- and diacylglycerols in essentially quantitative yields. Stoichiometric amounts of free fatty acids may be used, i.e. 3 molar equivalents as based on glycerol or 1 molar equivalent as based on number of mol equivalents of hydroxyl groups present in the glycerol moiety. Only 10% dosage of lipase as based on total weight of substrates is needed, which can be used a number of times. This is very important from the productivity point of view. All this, together with the fact that no solvent is required, renders this process a high feasibility from the scaling-up and industrialization point of view, since the cut in volume and bulkiness is enormous. Also, a slight excess (<5/5) of free fatty acids may be used in order to speed up the reaction toward the end and ensure a completion of the reaction.

At the initiation of the reaction, the 1- or 3-mono-acyglyeride is formed first, followed by the 1,3 diacylglyeride, and finally the triglyceride at the more extended reaction times. The mono- and diacylglyerides are useful intermediates in that they manifest biological activity, but have greater solubility in aqueous cellular environments and can participate in alternative molecular synthetic pathways such as synthesis of phospholipids or other functional lipids. In contrast, triglycerides are frequently deposited intact in cell membranes or storage vesicles. Thus, the administration of CLA in mono-, di- or triglycerol form rather than free fatty acid or ester, may influence the mode and distribution of uptake, metabolic rate and structural or physiological role of the CLA component.

III. Stabilization of CLA Compounds

The present invention also contemplates stabilization of CLA containing compounds, including but not limited to, CLA, esters of CLA, and triglycerides of CLA by preventing oxidation of the compounds. The present invention is not limited to any one mechanism. Indeed, an understanding of the mechanism of the invention is not necessary to produce the composition or perform the methods of the present invention. Nevertheless, unlike non-conjugated fatty acids, CLA does not appear to form peroxide breakdown products. This was demonstrated experimentally by measuring peroxide values (PV) spectrophotometrically by a chlorimetirc ferric thiocyanate method. After storage in open glass, the PV of CLA was 32; in comparison, the value for linoleic acid was 370.

CLA forms volatile organic compounds during breakdown, including hexane. Products stored in a steel drum for several weeks were found to contain up to 25 ppm hexane. Hexane has a characteristic taste and smell that is undesirable in food products. Oxidation of CLA appears to be caused by the presence of metal contaminants. Thus, a system for removal of such compounds that promote oxidation during purification is advantageous.

Furthermore, it is also advantageous to add compounds to CLA preparations to decrease oxidation during storage. Compounds that prevent oxidation (antioxidants) have two general mechanisms of action. The first is the prevention of oxidation by lipid peroxide radical scavenging. Examples include but are not limited to tocopherols and ascorbylpalmitate. The second mechanism for preventing oxidation is by the chelation of metal ions. Examples of metal oxidant chelators include, but are not limited to, citric acid esters and lecithin. Some commercially available compounds (e.g., Controx, Grumau (Henkel), Illertissen, DE) include both peroxide scavengers and metal chelators (e.g., lecithin, tocopherols, ascorbylpalmitate, and citric acid esters). In some embodiment of the present invention, metal oxidant chelators are added to CLA containing compounds to prevent oxidation. In other embodiments, a combination of metal oxidant chelators and peroxide scavengers is included in the CLA composition.

In some embodiments, gas chromatography/mass spectroscopy is used in detect the presence of volatile organic breakdown products of CLA. In other embodiments, oil stability index (OSI) measurements are used to detect the presence of volatile organic breakdown products of CLA. In some embodiments of the present invention methods for the removal of pro-oxidants (e.g., iron) from CLA samples are provided. Methods include, but are not limited to distillation or by adsorption. In some embodiments of the present invention, compounds are added to prevent oxidation of CLA.

Example 12 illustrates the measurement of volatile organic compounds by gas chromatography followed by mass spectroscopy. CLA is prepared by the method of Example 11. GC/MS is performed and peaks are identified by using reference materials (e.g., Wiley reference search). Table 28 lists the compounds identified and their relative abundance. Volatile organic compounds identified include pentane, hexane, heptane, 2-butenal, ethanol, 3-methyl butanal, 4-methyl pentanone, hexanal, heptanal, 2-pentyl furan, and octanal. Example 12 illustrates that samples of CLA contain undesirable volatile organic compounds. It is understood by one skilled in the art that samples may contain additional volatile organic compounds, depending on the starting materials and the exact reaction conditions.

In one illustrative example, it is demonstrated that the production of volatile organic acids increases over time. Example 13 shows the relative amounts of pentane and hexane in a CLA solution before and after storage in open air at 60° C. for 21 days. The results are shown in Table 28. The amount of both pentane and hexane increased by approximately two fold after 21 days. This example illustrates that the level of volatile organic compounds present as oxidation products of CLA increases over time.

In preferred embodiments, precautions are taken during purification to prevent oxidation during storage. These precautions include the removal of compounds that serve as pro-oxidants, including but not limited to iron or other metals. In some embodiments, metals are removed by treating with adsorbing agents, including but not limited to bleaching earth, active charcoal zeolites, and silica. In other embodiments, the pro-oxidants are removed by distillation.

Example 16 provides an illustrative example of one method for adsorbing metals. In this example, silica is used as the adsorbing agent. A triacylglyceride prepared by the method of example 14 was first deodorized at an elevated temperature and pressure. The sample was then mixed with silica and heated under vacuum. The present invention is not intended to be limited to the adsorption conditions described in Example 16; other methods of adsorption known to those skilled in the art are contemplated.

In some embodiments, pro-oxidants are removed in a distillation process. An illustrative example is given in Example 14. In this example, distillation of a triacylglyceride of CLA is performed on a molecular distillation apparatus. Distillation is carried out at 150° C. and a pressure of $10^{-2}$ mbar. The present invention is not intended to be limited to the conditions described for distillation. Other temperatures and pressures are within the scope of the present invention.

In some embodiments, oxidation of CLA is prevented by the addition of metal oxidant chelators or peroxide scavengers to the finished product. In some embodiments, the amount of oxidation is measured by the oil stability index (OSI). The OSI (See e.g., AOCS official method Cd 12b-92)

is a measurement of an oil's resistance to oxidation. It is defined mathematically as the time of maximum change of the rate of oxidation. This rate can be determined mathematically. Experimentally, the OSI is calculated by measuring the change in conductivity of deionized water is which volatile organic acids (oxidation products) are dissolved. When performing OSI measurements, it is important to avoid contamination by trace amounts of metals, which can accelerate the oxidation process. This is generally accomplished by careful washing of all glassware used with a cleaning solution lacking chromate or surfactants. Water must be deionized and all solvents must be of a highly purified grade.

Figure 2:
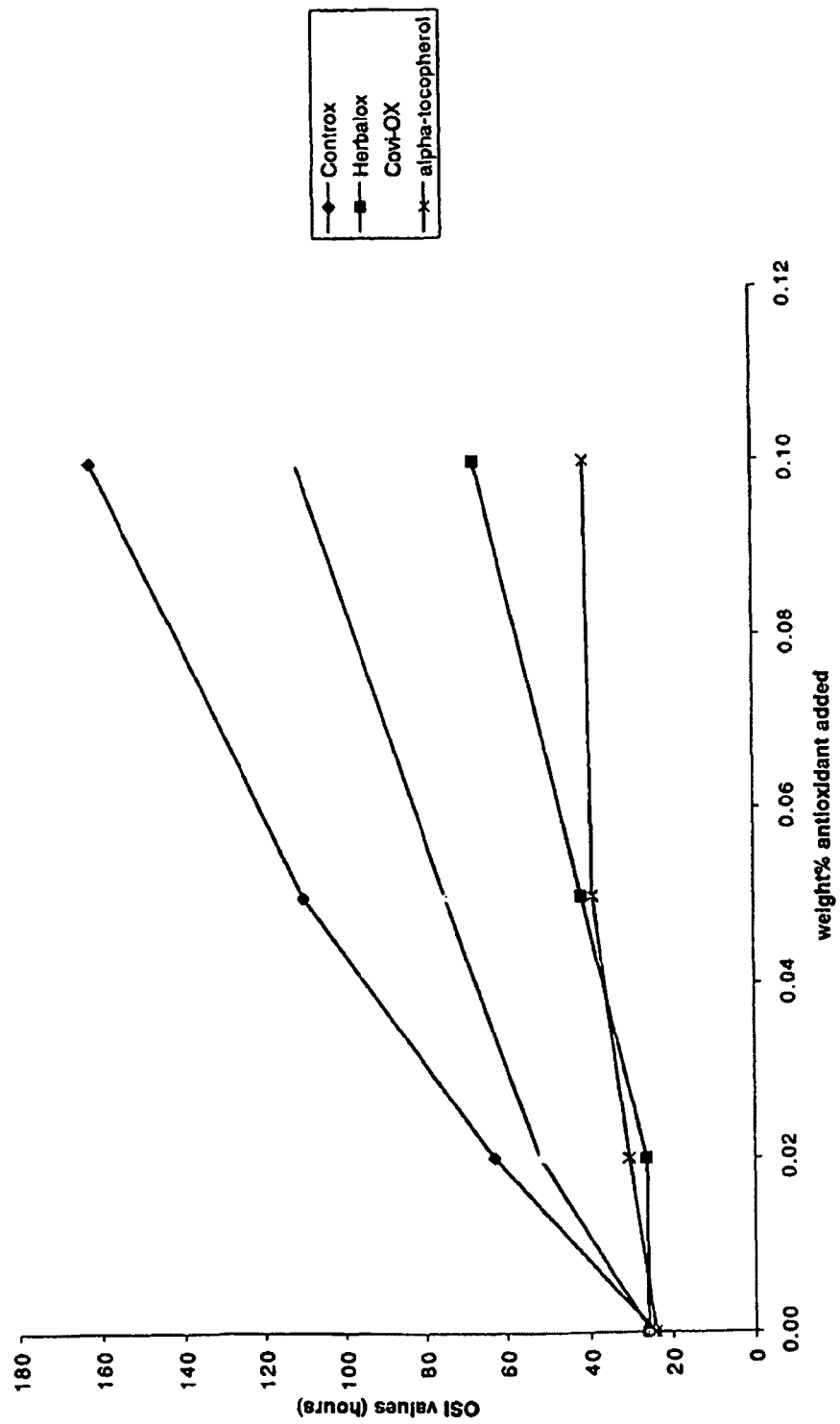
FIG. 2 is a graph of OSI values for CLA compositions in the presence of antioxidants.

An example illustrating OSI measurement of CLA in the presence or absence of antioxidants is given in Example 15. In Example 15, a triacyglyceride of CLA is prepared by the method of Example 14. Samples are placed in open dishes with varying amounts (0-0.1%) of four antioxidants (Controx Grunau (Henkel), Illertissen, DE), Herbalox (an extract of rosemary; Kalsec, Kalamazoo, Mich.), Covi-OX (Grunau (Henkel), Illertissen, DE), and alpha-tocopherol). The OSI is calculated as described above. Results are shown in Table 29 and FIG. 2. The addition of alpha-tocopherol did not significantly increase the OSI value. Herbalox increased the value by approximately 2-3 fold. Covi-OX and Controx increased the OSI values by a greater amount, approximately 4 and 6 fold, respectively. This experiment demonstrated that the addition of antioxidants can slow the oxidation of CLA containing compounds during storage.

IV. Administration of CLA Containing Compounds

The conjugated linoleic moieties of the present invention may be provided in a variety of forms. In some embodiments, administration is oral. The CLA moieties may be formulated with suitable carriers such as starch, sucrose or lactose in tablets, pills, dragees, capsules, solutions, liquids, slurries, suspensions and emulsions. Preferably, the CLA formulations contain antioxidants, including, but not limited to Controx, Covi-OX, lecithin, and oil soluble forms of vitamin C (ascorbyl palmitate). The CLA may be provided in aqueous solution, oily solution, or in any of the other forms discussed above. The tablet or capsule of the present invention may be coated with an enteric coating which dissolves at a pH of about 6.0 to 7.0. A suitable enteric coating which dissolves in the small intestine but not in the stomach is cellulose acetate phthalate. In some embodiments, the CLA is provided as soft gelatin capsules containing 750 mg 80% CLA (Tonalin™). The CLA may also be provided by any of a number of other routes, including, but not limited to, intravenous, intramuscular, intra-arterial, intramedullary, intrathecal, intraventricular, transdermal, subcutaneous, intraperitoneal, intranasal, enteral, topical, sublingual or rectal means. Further details on techniques for formulation for and administration and administration may be found in the latest edition of *Remington's Pharmaceutical Sciences* (Maack Publishing Co., Easton, Pa.).

An effective amount of CLA moiety may also be provided as a supplement in various food products, including animal feeds, and drinks. For the purposes of this application, food products containing CLA means any natural, processed, diet or non-diet food product to which exogenous CLA has been added. The CLA may be added in the form of free fatty acids, esters of conjugated linoleic acid, or as an oil containing partial or whole triglycerides of CLA. Therefore, CLA may be directly incorporated into various prepared food products, including, but not limited to diet drinks, diet bars, supplements, prepared frozen meals, candy, snack products (e.g., chips), prepared meat products, milk, cheese, yogurt and any other fat or oil containing foods. Food products formulated with alkyl esters or conjugated linoleic acid moieties produced by alkali alcoholate catalysts contain alcohols (e.g., methyl or ethyl alcohol) depending on the solvents and catalysts utilized. Generally, the alcohols will be present at about 1 to 10 ppm.

Furthermore, as shown above and in the Examples, CLA compositions can contain levels of volatile organic compounds that cause the taste and smell of food products containing the CLA to be adversely effected. It is contemplated that the food products of the present invention that contain CLA compositions having less than 100 ppm volatile organic compounds, and preferably less than 5 ppm volatile organic compounds, are superior in taste and smell to food products containing higher levels of volatile organic compounds and will be preferred in blind taste and smell tests. Accordingly, some embodiments of the present invention provide a food product containing a conjugated linoleic acid moiety, wherein the conjugated linoleic acid moiety has a sufficiently low volatile organic acid compound concentration so that taste and smell of the food product is not affected.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); µM (micromolar); kg (kilograms); g (grams); mg (milligrams); µg (micrograms); ng (nanograms); L or l (liters); ml (milliliters); µl (microliters); cm (centimeters); mm (millimeters); nm (nanometers); ° C. (degrees centigrade); KOH (potassium hydroxide); HCL (hydrochloric acid); Hg (mercury).

Example 1

Isomerization of Safflower Oil Using Propylene Glycol at Low Temperature

Safflower oil was isomerized in propylene glycol at low temperatures using KOH as a catalyst. The isomerization apparatus consisted of a two-necked flask with a thermometer placed in one neck, leaving a small opening to release excess pressure. A nitrogen supply was attached to the other neck of the flask. Solutions added to the flask were agitated by the use of a magnetic bar and a magnetic stirrer. The temperature of the flask was controlled by placing the flask in a thermostat-controlled oil bath placed on the magnetic stirrer.

The flask was filled with 60.27 g propylene glycol and 28.20 g KOH and immersed into the oil bath. The temperature was increased to 130° C. to dissolve the KOH. After the KOH had dissolved, 60.09 g of safflower oil was introduced into the flask. A high volume of nitrogen was circulated through the two-neck flask for 5 min. and then reduced to a lower volume. The mixture was heated to 150° C., which took approximately 40 min. The mixture was then allowed to react at 150° C. for 3.5 hours. At intervals, 3 ml samples were withdrawn for analysis.

The samples were placed directly into 6 ml of hot water and citric acid was added in excess until the free fatty acids separated out as the top layer. Heating was necessary to prevent solidification while the citric acid was added. To convert the free fatty acids into methylesters for analysis by Gas Chromatography, 0.025 g of the free fatty acids, 5 ml of a 4% solution of HCl and ethanol were added to a test tube. Nitrogen was added to the tube, then the tube was sealed and placed in a water bath at 60° C. for 20 min. The tube was then cooled and 1 ml purified water and 5 ml isooctane were added. Nitrogen was added to the tube and the tube was shaken for 30 seconds. The resulting upper layer was added to 1 µl of purified water in a new test tube and again shaken under nitrogen. The resulting upper layer was then washed of isooctane and decanted into a third test tube. A small amount of sodium sulfate was added for water absorption. A 1 µl sample was then injected directly into the Gas chromatograph.

The gas chromatography conditions were as follows:

| | |
|---|---|
| System: | Perkins-Elmer Auto System |
| Injector: | Splitless at 240° C. |
| Detector: | Flame Ionization Detector at 280° C. |
| Carrier: | Helium |
| Column: | WCOT Fused Silica 0.25 mm X100M, CP-SL 88 for FAME, DF 0.2 |
| Oven Program: | 80° C. (0 min.) increasing to 220° C. at 10° C. per min. and held at 220° C. for 10 min. |

All results are expressed as the relative peak area percentage. Standards are generally unavailable, so the peaks which eluted were verified with other systems. GC-MS determines the number, but not the position of cis and trans bonds. Therefore, NMR analysis was used to verify the bond positions. The main peaks were c9,t11 and t10,c12. For NMR analysis of CLA isomers, please see Marcel S. F. Lie Ken Jie and J. Mustafa, Lipids, 32 (10) 1019-34 (1997), incorporated herein by reference.

This data, presented in Table 6 and summarized in Table 10, demonstrates that isomerization of safflower oil using polypropylene glycol as a solvent, KOH as a catalyst, and low temperatures results in the production of conjugated linoleic acid lacking 8,10 and 11,13 isomers. The highly polar columns utilized in this experiment may be successfully used to separate the 8,10 and 11,13 isomers from c9,t11 and t10,c12 isomers. The 8,10 isomers tend to coelute or elute just after the c9,t11 isomer. The 11,13 isomer elutes in front of the t10,c11 isomer or coelutes with the t10,c12 isomer, depending on the column conditions.

The conjugated linoleic acid produced according to this method by characterized by comparing the various isomers produced. First, the isomerization reaction went essentially to completion. The completeness of the reaction is obtained by dividing the total peak area the for linoleic acid isomers minus residual c9, t12 linoleic acid by the total peak area. This value is 0.994. Second, the ratio of c9,t11 and t10,c12 isomers to total peak area may be determined. This value is 0.953. Third, the ratio of the t9,t11 and t10,t12 isomers to the c9,t11 and t10,c12 isomers may be determined. This value is 0.010. Fourth, the ratio of the t9,t11 and t10,t12 isomers to total peak area may be determined. This value is 0.009. Fifth, the ratio of the t10,c12 isomer to the c9,t11 isomer may be determined. This value is 1.018. These ratios are summarized in Table 11.

Example 2

Aqueous Isomerization at High Temperature and Pressure

Fifty grams of water and 25.32 g NaOH were added to a high pressure reactor (Parr Model 450 ML Benchtop Alloy 400, equipped with a pressure gauge and stirrer.) The NaOH was allowed to dissolve and 94.0 g safflower oil was added to the reactor. The reactor was closed and flushed for 2 min. with nitrogen and then all valves were closed. The reactor was heated in an electrical gasket to 210° C. and maintained at that temperature for 6 hours. The temperature was then reduced to 60° C. before pressure was released and the reactor opened. Two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography as in Example 1.

The results of the gas chromatography are presented in Table 7 and summarized in Table 10. These data indicate that this isomerization method results in the formation of relatively high amounts of the 8,10 and 11,13 isomers. Ratios are presented in Table 11.

Example 3

Non-Aqueous Alkali Isomerization of Safflower Oil at High Temperature and Pressure 100.48 g propylene glycol and 46.75 g of KOH were added to a high-pressure reactor as described in Example 2. The reactor was then heated to 130° C. to dissolve the KOH. 100.12 g of safflower oil were then added to the KOH-propylene glycol mixture. The reactor was closed, flushed for 1 min. with nitrogen, and all valves closed. The reactor was then heated to 210° C. and maintained at that temperature for 1 hour. The reactor was cooled and the contents decanted into 120 g of hot water. While stirring, 35.3 g 37% HCl and 27.59 g citric acid were serially added to the fatty acids. A sample was taken from the top layer and dried in a vacuum flask at 60° C. A sample of the resulting fatty acids was analyzed by gas chromatography as described in Example 1.

The results are presented in Table 8 and summarized in Table 10. This experiment demonstrates that isomerization of safflower oil with KOH and a non-aqueous solvent at high temperature results in the formation of significant amounts of 8,10 and 11,13 isomers, as well as t9,t11 and t10,t12 isomers. Ratios are presented in Table 11.

Example 4

Aqueous Alkali Reaction at Low Temperature 49.94 g water and 39.96 g NaOH were added to a high-pressure reactor as described in Example 3. This mixture was heated until the NaOH dissolved. Next, 100.54 g of safflower oil was added to the high-pressure reactor, the reactor was flushed with nitrogen, and all valves closed. The high-pressure reactor was heated to 179° C. for 22.5 hours. Samples were prepared for Gas Chromatography as in Example 3. The data is provided in Table 9 and summarized in Table 10. This experiment demonstrates that when low temperatures are used for aqueous alkali isomerization, the conjugation reaction does not go to completion. Furthermore, significant amounts of the 8,10 and 11,13 isomers are produced. Ratios are presented in Table 11.

TABLE 6

| Peak # | Time (Min) | Component Name | Area (%) | Area (µV · s) | Height (µV) |
|---|---|---|---|---|---|
| 1 | 38.164 | | 0.08 | 4101.65 | 622.28 |
| 2 | 49.539 | C16:0 | 6.29 | 335897.80 | 32745.95 |
| 3 | 53.107 | C16:1 | 0.06 | 3240.60 | 447.82 |
| 4 | 61.620 | C18:0 | 2.38 | 127182.30 | 12999.14 |
| 5 | 64.821 | C18:1 c9 | 12.34 | 659111.72 | 52209.40 |
| 6 | 65.254 | | 0.57 | 30402.68 | 3475.09 |

TABLE 6-continued

| Peak # | Time (Min) | Component Name | Area (%) | Area (μV·s) | Height (μV) |
|---|---|---|---|---|---|
| 7 | 67.263 | | 0.11 | 5757.35 | 758.08 |
| 8 | 67.940 | | 0.10 | 5523.00 | 700.44 |
| 9 | 68.755 | | 0.24 | 12816.90 | 1543.27 |
| 10 | 69.310 | | 0.22 | 11803.80 | 1430.59 |
| 11 | 69.846 | C18:2 c9,c12 | 0.44 | 23336.75 | 2500.24 |
| 12 | 73.618 | | 0.28 | 14828.70 | 1838.66 |
| 13 | 76.621 | | 0.16 | 8400.65 | 1050.19 |
| 14 | 77.388 | CLA c9,t11 | 36.51 | 1950669.98 | 124313.83 |
| 15 | 78.370 | CLA t10,c12 | 37.16 | 1985488.96 | 132265.33 |
| 16 | 78.664 | CLA c9,c11 | 1.06 | 56583.10 | 5699.43 |
| 17 | 78.880 | CLA c10,c12 | 1.26 | 67503.55 | 4572.65 |
| 18 | 80.102 | CLA t9,t11/ t10,t12 | 0.73 | 39110.00 | 4743.28 |
| 19 | 85.165 | | 0.03 | 1621.65 | 231.32 |
| | | | 100.00 | 5343381.15 | 384147.01 |

TABLE 7

| Peak # | Time (Min) | Component Name | Area (%) | Area (μV·s) | Height (μV) |
|---|---|---|---|---|---|
| 1 | 36.554 | | 0.09 | 4122.05 | 627.02 |
| 2 | 47.785 | C16:0 | 6.68 | 290571.30 | 28224.34 |
| 3 | 51.280 | C16:1 | 0.07 | 3188.05 | 425.57 |
| 4 | 59.787 | C18:0 | 2.63 | 114362.95 | 12678.63 |
| 5 | 62.923 | C18:1 c9 | 13.12 | 570712.08 | 42259.71 |
| 6 | 63.346 | | 0.72 | 31329.22 | 3774.35 |
| 7 | 65.355 | | 0.54 | 23620.70 | 2848.31 |
| 8 | 66.034 | | 0.67 | 28980.78 | 3333.95 |
| 9 | 66.574 | | 0.10 | 4370.91 | 594.22 |
| 10 | 66.811 | | 0.35 | 15045.61 | 1469.30 |
| 11 | 67.352 | | 0.41 | 18002.20 | 2035.53 |
| 12 | 67.889 | C18:2 c9,c12 | 1.43 | 62002.15 | 6714.22 |
| 13 | 69.200 | | 0.09 | 3840.85 | 474.10 |
| 14 | 71.680 | | 0.30 | 13099.10 | 1744.21 |
| 15 | 74.640 | | 1.62 | 70689.87 | 4117.23 |
| 16 | 75.310 | CLA c9,t11/ 8,10 | 24.87 | 1082087.96 | 57619.24 |
| 17 | 76.032 | CLA 11,13 | 14.72 | 640440.14 | 42975.86 |
| 18 | 76.277 | CLA t10,c12 | 16.00 | 695923.85 | 63512.81 |
| 19 | 76.450 | CLA c8,c10 | 1.26 | 54676.10 | 7614.29 |
| 20 | 76.626 | CLA c9,c11 | 2.08 | 90411.44 | 10891.36 |
| 21 | 76.881 | CLA c10,c12 | 3.00 | 130593.96 | 11727.80 |
| 22 | 77.022 | CLA c11,c13 | 1.77 | 77065.69 | 9906.74 |
| 23 | 77.477 | | 0.66 | 28867.85 | 3322.69 |
| 24 | 77.868 | | 0.63 | 27391.94 | 2934.68 |
| 25 | 78.173 | CLA t9,t11/t10,t12 | 6.00 | 260985.40 | 26124.10 |
| 26 | 83.140 | | 0.12 | 5164.40 | 586.21 |
| 27 | 85.878 | | 0.06 | 2735.80 | 347.01 |
| | | | 100.00 | 4350282.35 | 348883.46 |

TABLE 8

| Peak # | Time (Min) | Component Name | Area (%) | Area (μV·s) | Height (μV) |
|---|---|---|---|---|---|
| 1 | 38.249 | | 0.08 | 3999.70 | 599.26 |
| 2 | 49.639 | C16:0 | 6.41 | 333807.80 | 32279.13 |
| 3 | 53.218 | C16:1 | 0.06 | 3123.00 | 427.39 |
| 4 | 55.508 | | 0.03 | 1322.20 | 190.60 |
| 5 | 61.753 | C18:0 | 2.55 | 132854.50 | 14939.09 |
| 6 | 64.104 | C18:1 c9 | 0.03 | 1640.30 | 245.73 |
| 7 | 64.950 | | 12.92 | 672672.91 | 53345.47 |
| 8 | 65.382 | | 0.64 | 33297.29 | 3728.28 |
| 9 | 65.783 | | 0.03 | 1411.20 | 219.76 |
| 10 | 67.403 | | 0.62 | 32194.66 | 2836.09 |
| 11 | 67.793 | | 0.24 | 12660.05 | 1495.10 |
| 12 | 68.088 | | 0.68 | 35371.43 | 3210.82 |
| 13 | 68.421 | | 0.07 | 3684.10 | 473.77 |
| 14 | 68.635 | | 0.04 | 1948.63 | 257.65 |
| 15 | 68.890 | | 0.29 | 14979.18 | 1499.63 |
| 16 | 69.192 | | 0.04 | 2268.69 | 324.39 |
| 17 | 69.430 | | 0.25 | 13028.21 | 1369.93 |
| 18 | 69.947 | C18:2 c9,c12 | 0.23 | 11895.70 | 1125.77 |
| 19 | 70.341 | | 0.02 | 1168.20 | 196.75 |
| 20 | 73.741 | | 0.31 | 15930.60 | 1965.82 |
| 21 | 75.448 | | 0.08 | 3906.00 | 387.98 |
| 22 | 76.768 | | 1.79 | 93172.74 | 6637.34 |
| 23 | 77.002 | | 0.63 | 32882.76 | 5024.06 |
| 24 | 77.389 | CLA c9,t11/ 8,10 | 15.62 | 813447.45 | 57234.62 |
| 25 | 77.735 | | 1.92 | 99754.50 | 8641.88 |
| 26 | 78.045 | CLA 11,13 | 4.03 | 209728.35 | 19826.20 |
| 27 | 78.335 | CLA t10,c12 | 12.63 | 657681.44 | 62016.93 |
| 28 | 78.566 | CLA c8,c10 | 0.64 | 33432.80 | 5277.06 |
| 29 | 78.727 | CLA c9,c11 | 2.21 | 114935.49 | 10791.54 |
| 30 | 79.079 | CLA c10,c12 | 3.98 | 207339.28 | 12766.61 |
| 31 | 79.663 | CLA c11,c13 | 1.40 | 73036.34 | 6275.58 |
| 32 | 80.516 | CLA t9,t11/ t10,t12 | 29.39 | 1529956.09 | 100323.85 |
| 33 | 82.318 | | 0.03 | 1563.70 | 230.42 |
| 34 | 85.289 | | 0.07 | 3657.50 | 423.53 |
| 35 | 88.093 | | 0.05 | 2368.50 | 301.03 |
| | | | 100.00 | 5206121.30 | 416889.05 |

TABLE 9

| Peak # | Time (Min) | Component Name | Area (%) | Area (μV·s) | Height (μV) |
|---|---|---|---|---|---|
| 1 | 38.154 | | 0.09 | 3371.70 | 501.86 |
| 2 | 49.501 | C16:0 | 6.80 | 253221.00 | 25807.11 |
| 3 | 53.100 | C16:1 | 0.07 | 2723.55 | 353.01 |
| 4 | 55.391 | | 0.03 | 1078.10 | 142.65 |
| 5 | 61.618 | C18:0 | 2.68 | 100015.20 | 11002.94 |
| 6 | 63.990 | | 0.03 | 946.40 | 156.50 |
| 7 | 64.791 | C18:1 c9 | 13.13 | 489016.55 | 38313.02 |
| 8 | 65.270 | | 0.69 | 25645.55 | 2670.46 |
| 9 | 67.296 | | 0.12 | 4466.65 | 558.35 |
| 10 | 67.960 | | 0.11 | 4012.70 | 517.76 |
| 11 | 68.800 | | 0.37 | 13840.49 | 1314.91 |

TABLE 9-continued

| Peak # | Time (Min) | Component Name | Area (%) | Area (µV · s) | Height (µV) |
|---|---|---|---|---|---|
| 12 | 69.370 | | 0.30 | 11141.11 | 1245.85 |
| 13 | 70.001 | C18:2 c9,c12 | 20.52 | 764287.35 | 62474.10319.72 |
| 14 | 73.538 | | 0.30 | 11075.20 | 1357.19 |
| 15 | 76.519 | | 0.42 | 15662.14 | 1154.22 |
| 16 | 77.231 | CLA c9,t11/8,10 | 22.45 | 836230.58 | 56972.76 |
| 17 | 77.911 | CLA 11,13 | 7.56 | 281633.54 | 24467.27 |
| 18 | 78.197 | CLA t10,c12 | 19.77 | 736384.86 | 66688.46 |
| 19 | 78.559 | CLA c8,c10 | 1.21 | 45158.40 | 3837.29 |
| 20 | 78.787 | CLA c9,c11 | 0.87 | 32564.06 | 3409.07 |
| 21 | 78.953 | CLA c10,c12 | 0.89 | 33053.57 | 2499.70 |
| 22 | 79.413 | CLA c11,c13 | 0.12 | 4453.10 | 353.06 |
| 23 | 79.792 | | 0.13 | 4936.60 | 436.59 |
| 24 | 80.052 | CLA t9,t11/t10,t12 | 1.13 | 42203.55 | 4550.59 |
| 25 | 82.298 | | 0.03 | 981.60 | 150.46 |
| 26 | 82.946 | | 0.03 | 1107.95 | 151.48 |
| 27 | 85.135 | | 0.10 | 3639.90 | 383.36 |
| 28 | 87.927 | | 0.06 | 2212.50 | 254.61 |
| | | | 100.00 | 3725063.90 | 311570.23 |

TABLE 10

Relative Area Percentage

| Isomer | Example 1 | Example 2 | Example 3 | Example 4 |
|---|---|---|---|---|
| c9,t12 | 0.44 | 1.43 | 0.23 | 20.52 |
| c9,t11 | 36.51 | na | na | na |
| c9,t11/8,10 | <0.5* | 24.87 | 15.62 | 22.45 |
| t10,c12 | 37.16 | 16.00 | 12.63 | 19.77 |
| c9,c11 | 1.06 | 2.08 | 2.21 | 0.87 |
| c8,c10 | <0.5 | 1.26 | 0.64 | 1.21 |
| c10,c12 | 1.26 | 3.00 | 3.98 | 0.89 |
| t9,t11/t10,t12 | 0.73 | 6.00 | 29.39 | 1.13 |
| 11,13 | <0.5 | 10.23 | 4.05 | 7.65 |
| c11,c13 | <0.5 | 1.77 | 1.40 | 0.12 |
| Unidentified | <0.5 | 2.91 | 4.34 | 0.55 |
| CLA Total | 76.88 | 72.61 | 74.24 | 54.55 |
| Total area | 77.32 | 74.04 | 74.47 | 75.07 |

*total percentage of 8,10 is less than 0.5 na - value is reflected as component of c9,t11/8,10

TABLE 11

| Isomer Ratio | | Example 1 | Example 2 | Example 3 | Example 4 |
|---|---|---|---|---|---|
| Total CLA isomer | Total peak area | 0.994 | 0.981 | 0.997 | 0.727 |
| c9,t11-t10,c12 | Total peak area | 0.953 | 0.552* | 0.379* | 0.562* |
| t9,t11-t10,t12 | c9,t12-t10,c12 | 0.010 | 0.147* | 1.040* | 0.027* |
| t9,t11-t10,t12 | Total peak area | 0.009 | 0.081 | 0.395 | 0.015 |
| Total 11,13 | Total peak area | na | 0.223 | 0.073 | 0.102 |
| t10,c12 | c9,t11 | 1.018 | 1.554* | 0.809* | 0.881* |

*c9,t11 includes 8,10 isomer na - no 11,13 detected

Example 5

The Preparation of Triacylglycerols of CLA by Direct Esterification

General. H nuclear magnetic resonance spectra were recorded on a Bruker AC 250 NMR spectrometer in deuterated chloroform as a solvent. HPLC separations were carried out by a PrepLC™ System 500A instrument from Waters using the PrepPak® 500/Silica Cartridge column from Millipore, eluting with 10% diethyl ether in petroleum ether. Analytical GLC was conducted on a Perkin-Elmer 8140 Gas Chromatograph according to a previously described procedure, as described in Haraldsson, et al, Acta Chem Scanned 45: 723 (1991).

The immobilized *Candida antarctica* lipase was provided by Novo Nordisk in Denmark as Novozyme™. It was used directly as provided in the esterification experiments. Analytical grade diethyl ether purchased from Merck was used without any purification, but synthetic grade n-hexane also from Merck was freshly distilled prior to use in extractions and HPLC chromatography. Glycerol (99%) was purchased from Sigma and Aldrich Chemical Company and used without further purification. The CLA concentrate was provided by Natural Lipids in Norway as free fatty acids as Tonalin™. Its purity was confirmed by analytical GLC and high-field NMR spectroscopy which revealed some glyceride impurities. The CLA concentrate was found to contain 43.3% 9-cis, 11-trans-linoleic acid, 44.5% 10-trans,12-cis-linoleic acid, 5.4% of other CLA isomers, 5.6% oleic acid and 0.6% each of palmitic and stearic acid as determined by GLC at the Science Institute.

Example 6

The Preparation of Triacylglycerols of CLA by Direct Esterification

Immobilized *Candida antarctica* lipase (1.25 g) was added to a mixture of glycerol (1.22 g. 13.3 mmol) and CLA as free fatty acid (M.wt.280.3 g/mol; 11.6 g, 41.5 mmol). The mixture was gently stirred on a magnetic stirrer hot plate at 65° C. under continuous vacuum of 0.01-0.5 Torr. The volatile water produced during the progress of the reaction was continuously condensed into liquid nitrogen cooled traps. After 48 h the reaction was discontinued, n-hexane added and the enzyme separated off by filtration. The organic phase was treated with an alkaline aqueous solution of sodium carbonate to remove excessive free fatty acids (when required). The organic solvent (after drying over anhydrous magnesium sulfate when appropriate) was removed in vacuo on a rotary evaporator followed by high-vacuum treatment to afford the virtually pure product as a slightly yellowish oil (10.9 g; average M.wt.878.6 g/mol; 93% yield). When stoichiometric amounts of free fatty acids were used, titration by standardized sodium hydroxide was applied to determine the free fatty acid content of the crude reaction product (less than 1% free fatty acid content as based on number of mol of ester groups, corresponding to at least 99% incorporation, which is equivalent to the minimum of 97% triglyceride content). The crude product was directly introduced into HPCL eluting with 10% diethylether in n-hexane to afford 100% pure triglyceride as a colourless oil. 250 MHz 1H NMR (CDCl3) δ (ppm) 6.35-6.23 (3H, ddt, Jtrans=15.0 Hz, J=10.9 Hz, Jallyl=1.3, =CHCH=CH), 5.98-5.90 (3H, dd, Icis=10.9, J=10.9, —CH=CHCH=), 5.71-5.59 (3H, dtd, Jtrans=15.0 Hz, J=6.9 Hz, J=6.9 Hz, J=2.2 Hz, =CH=CHCH2-), 5.35-5.26 (4H, m, =CH2CH=CH— and —CH2C—ICH2-), 4.33-4.26 (2H, dd, Jgem=11.9 Hz, J=4.3, —CH2CHCH2-), 4.18-4.102H, dd, Jgem=1.8 Hz, J=6.0, —CH2CHCH2-), 2.37-2.31 (6H, t, J=7.4H2, —CH2COOR), 2.19-2.05 (12H, m, —CH2CH=CH—), 1.66-1.60 (6H, qu., J=Hz, —CH2CH2COOR), 1.43-1.30 (18H, m, —CH2-), 0.91-0.86 (9H, t, J=6.7 Hz, —CH3). $^{13}$C-NMR (CDCl$_3$): δ (ppm) 173.2, 172.8, 134.6, 130.0, 128.6, 125.5, 68.8, 62.0, 34.0, 32.9, 31.6, 29.6-28.9 (6C), 27.6, 24.8, 22.5, 14.1.

In order to monitor the progress of the reaction and provide more details about the composition of individual glycerides during the reaction, samples were collected regularly as the reaction proceeded. They were analyzed by HNMR spectroscopy and provided a good insight into the composition of mono-, di- and triacylglycerols during the progress of the reaction. The results are demonstrated in Table 12 below. As can be noticed from the table, 1,3-diacylglycerols dominated the reaction mixture during the first two hours of the reaction. After 4 hours triacylglycerols took over and had reached 98% composition after 22 hours and 100% after 48 hours. As would be expected 1,2-diacylglycerols reached considerably lower levels than the 1,3-diacylglycerols. 1-monoacylglycerols reached a maximum during the first hour of the reaction, but 2-monoacylglycerols were not detected throughout the reaction.

TABLE 12

| Time | % Incorporation | | | | Residual FFA |
|---|---|---|---|---|---|
| h | 1-MG | 1,2-DG | 1,3-DG | TG | % |
| 0 | 0 | 0 | 0 | 0 | 100 |
| 1 | 8.3 | 15.2 | 39.4 | 7.8 | 29.3 |
| 2 | 2.7 | 9.3 | 46.5 | 17.4 | 24.1 |
| 4 | 1.7 | 7.9 | 25.4 | 49.4 | 15.5 |
| 6 | 0.5 | 5.2 | 16.0 | 68.1 | 10.1 |
| 8 | 0.0 | 3.9 | 9.9 | 80.5 | 5.7 |
| 10 | 0.0 | 3.0 | 7.0 | 85.8 | 4.2 |
| 12 | 0.0 | 2.7 | 5.6 | 89.2 | 2.5 |
| 22 | 0.0 | 1.0 | 1.4 | 95.8 | 1.8 |
| 48 | 0.0 | 0.0 | 0.0 | 100 | 0.0 |

Example 7

Effect of Varying Temperature and Reaction Duration on CLA Yield and Composition The effect of temperature and reaction duration on the conjugation of safflower oil was determined. Water and NaOH were added to a high pressure reactor (Parr Model 450 ML Benchtop Alloy 400, equipped with a pressure gauge and stirrer) as indicated in Table 1, columns 1 and 2. The NaOH was allowed to dissolve and safflower oil (column 3) was added to the reactor. The reactor was closed and flushed for 2 min. with nitrogen and then all valves were closed. The reactor was heated in an electrical gasket to the desired temperature (column 4) and maintained at that temperature for the desired time (column 5). The temperature was then reduced to 60° C. before pressure was released and the reactor opened. For each reaction, two grams of the resulting solidified soap were taken from the reactor and dissolved in water at approximately 40° C. Citric acid was then added to reduce the pH of the solution to below 6. A sample was withdrawn from the fatty acid top layer and prepared for Gas Chromatography.

The results of the gas chromatography are presented in column 6 (total percentage of 9,11 and 10,12 isomers), column 7 (total percentage of 11,13 isomers), and column 8 (total percentage of all CLA isomers or yield). These data indicate that as reaction duration and temperature increase, the total amount of conjugation and the percentage of 11,13 isomers increase. Under conditions where formation of the 11,13 isomer is low, the total amount of conjugation is also low.

TABLE 13

| Water gram | NaOH gram | Safflower Oil gram | Mean t. °C. of reaction | Time hours | 9,11 + 10,12 area % | 11,13 area % | CLA total area % |
|---|---|---|---|---|---|---|---|
| 50.21 | 29.93 | 99.94 | 189 | 6.36 | 45.99 | 5.73 | 55.86 |
| 70.20 | 29.93 | 99.94 | 187 | 6.40 | 44.94 | 3.23 | 51.28 |
| 50.10 | 30.17 | 100.74 | 183 | 6.39 | 40.23 | 3.37 | 48.07 |
| 49.91 | 29.93 | 100.40 | 179 | 6.52 | 32.00 | 1.48 | 34.92 |
| 49.97 | 29.80 | 100.02 | 179 | 10.08 | 41.86 | 3.12 | 48.21 |
| 49.94 | 39.84 | 99.84 | 179 | 6.30 | 32.6 | 3.04 | 37.12 |
| 29.50 | 24.83 | 99.21 | 240 | 3.25 | 28.37 | 10.78 | 71.58 |
| 30.33 | 25.15 | 100.43 | 221 | 2.30 | 40.87 | 14.72 | 72.61 |
| 49.92 | 30.00 | 100.36 | 150 | 6.34 | 7.07 | 0 | 7.44 |

Example 8

Conjugation of Safflower Fatty Acid Methylester (FAME)

The reaction was carried out in a closed vessel. The following components were mixed together: 100 g safflower FAME and a mixture of approximately 2.8 g KOCH$_3$ and 2.8 g methanol. There was probably more KOMe than methanol due to evaporation of methanol during mixing of the two components. The mixture was stirred for 5 hours at 111-115 deg C. in nitrogen atmosphere in a closed reaction vessel. The distribution of isomers was analyzed by Gas Chromatography. The results are summarized in Table 2. The raw GC data is presented in Table 3. These data indicate that the conjugation safflower FAME may be accomplished under mild conditions, resulting in a product lacking appreciable amounts of undesirable 8,10 and 11,13 isomers.

TABLE 14

| Isomer Distribution | |
| --- | --- |
| Palmitic acid | 6.6% |
| Stearic acid | 2.7% |
| Oleic acid | 12.9% |
| Linoleic acid | 5.7% (unconjugated) |
| CLA c9,t11 | 34.1% |
| CLA t10,c12 | 33.3% |
| CLA c,c | 1.8% |
| CLA t,t | 1.0% |
| CLA total | 70.2% |

Example 9

Large Scale Batch Production of Conjugated Safflower FAME

The production of safflower conjugated FAME may be divided into two steps, methanolysis and conjugation. For methanolysis, 6,000 kg safflower oil was drawn into a closed reactor. The reactor was purged with nitrogen at atmospheric pressure, and 1150 liters of methanol and 160 kg of $NaOCH_3$ (30% solution) were added. The mixture is heated to 65° C. while stirring, and reacted at 65° C. for 2 hours. The resulting bottom layer was decanted while the reactor was purged with nitrogen gas. 1000 liters of water (40-50° C., into which 50 kg citric acid monohydrate has been dissolved) was then added while stirring. The layers were allowed to separate (approx. 60 min.) and the bottom layer decanted while purging the reactor with nitrogen gas. The resulting safflower FAME product was dried at 80° C. under vacuum for one hour.

To conjugate the safflower FAME, 250 kg of $KOCH_3$ dissolved in methanol to form a paste was added to the reactor. The mixture was then heated to 120° C. while stirring and the reaction allowed to continue for 3 hours. The mixture was cooled to 100° C., and 1000 liters of water (40-50° C., into which 50 kg citric acid monohydrate has been dissolved) was added while stirring. The mixture was stirred for 15 minutes and then the layers were allowed to separate for 20 minutes. The bottom layer was decanted and the product dried at 80° C. for 1 hour and then stored under nitrogen.

The resulting CLA was analyzed using a Perkin Elmer Autosystem XL GC under the following conditions:

| | |
| --- | --- |
| Column: | WCOT Fused Silica 100 m × 0.25 mm, Coating CP SIL 88 |
| Carrier: | He gas, 30.0 PSI |
| Temp: | 220 C. |
| Run time: | 35-90 min. |
| Inject.: | Splitless, 240 C. |
| Detect.: | FID, 280 C. |

The GC results are summarized in Tables 15 and 16.

TABLE 15

| Peak # | Time (min) | Component Name | Area (%) | Area (µVs) | Height (µV) |
| --- | --- | --- | --- | --- | --- |
| 1 | 46.874 | C16:0 | 6.37 | 29874.50 | 4026.29 |
| 2 | 58.685 | C18:0 | 2.61 | 12231.70 | 1542.34 |
| 3 | 62.141 | C18:1 c9 | 13.14 | 61668.78 | 7369.08 |
| 4 | 62.652 | | 0.70 | 3263.62 | 391.92 |
| 5 | 66.404 | | 0.35 | 1627.60 | 177.41 |
| 6 | 66.917 | | 0.26 | 1239.15 | 157.35 |
| 7 | 67.583 | C18:2 c9,c12 | 5.75 | 26964.95 | 3153.80 |
| 8 | 70.631 | | 0.25 | 1171.90 | 141.41 |
| 9 | 75.011 | CLA c9,t11 | 34.42 | 161529.90 | 17544.79 |
| 10 | 75.936 | CLA t10,c12 | 33.48 | 157129.82 | 17157.21 |
| 11 | 76.400 | CLA c9,c11 | 0.84 | 3935.70 | 302.61 |
| 12 | 76.631 | CLA c10,c12 | 0.49 | 2316.98 | 279.31 |
| 13 | 77.905 | CLA t,t9,11 + 10,12 | 1.35 | 6344.50 | 710.88 |
| | | | 100.00 | 469299.10 | 52954.41 |

Example 10

The following are examples of typical animal rations containing the CLA free fatty acids, triglycerides, and esters of the present invention.

A. Pig Starter Rations

TABLE 16

| Ingredients | lbs. | kgs. |
| --- | --- | --- |
| Corn, yellow (8.4% protein) | 1067 | 484.7 |
| Soy bean meal, solvent extracted, dehulled (47% protein) | 570 | 259 |
| CLA | 5 | 2.3 |
| Whey, dried (12.0% protein) | 300 | 136 |
| Dicalcium phosphate | 24 | 11 |
| Limestone | 16 | 7 |
| Iodized salt | 5 | 2 |
| Trace mineral premix | 5 | 2 |
| Vitamin premix | 8 | 4 |
| Totals | 2000 | 908 |

B. Grower-Finisher Rations for Pigs
(From 40-240 lbs[18-109 kgs])

TABLE 17

| Ingredients | lbs. | kgs. |
| --- | --- | --- |
| Corn, yellow (8.4% protein) | 1566 | |
| Soybean meal, solvent extracted (44% protein) | 380 | |
| CLA | 5 | |
| Dicalcium phosphate | 21 | |
| Limestone | 15 | |
| Iodized Salt | 5 | |
| Trace Mineral Premix | 3 | |
| Vitamin Premix | 3 | |
| Total | 2000 | |

C. Pig Grower Finisher Rations
(For Pigs 121-240 lbs[55-109 kgs])

TABLE 18

| Ingredients | lbs. | kgs. |
| --- | --- | --- |
| Corn, yellow (8.4% protein) | 1687 | |
| Soybean meal, solvent extracted (44% protein) | 265 | |
| CLA | 5 | |

TABLE 18-continued

| Ingredients | lbs. | kgs. |
| --- | --- | --- |
| Dicalcium phosphate | 18 | |
| Limestone | 15 | |
| Iodized salt | 5 | |
| Trace mineral premix | 2 | |
| Vitamin premix | 3 | |
| Total | 2000 | |

Composition and Analysis of Pig Trace Mineral Remix

TABLE 19

| Element | Source | Amount (lbs) |
| --- | --- | --- |
| Copper (Co) | Copper Sulfate | 1.500 |
| Iodine (I) | Potassium Iodide | 0.010 |
| Iron (Fe) | Ferrous Sulfate | 25.000 |
| Manganese (Mn) | Manganese Sulfate | 2.500 |
| Selenium (Se) | Sodium Selenite) | 0.025 |
| Zinc (Zn) | Zinc Sulfate | 25.000 |
| | Carrier | 45.965 |
| Total | | 100.000 |

Composition of Pig Vitamin Premix

TABLE 20

| Vitamins | Amount |
| --- | --- |
| Essential | |
| Vitamin A ... (million IU) | 5.0 |
| Vitamin D ... (million IU) | 0.6 |
| Vitamin E ... (thousand IU) | 26.0 |
| Niacin ... (g) | 25.0 |
| d-Pantothenic acid ... (g) | 20.0 |
| Riboflavin ... (g) | 6.0 |
| Vitamin B-12 ... (mg) | 25.0 |
| Optional | |
| Biotin ... (g) | 0.3 |
| Menadione ... (g) | 4.0 |
| Carrier ... | to 10 lbs |
| Total | 10.0 |

D. 18% Protein Layer Rations for Hens

TABLE 21

| Ingredients | lbs. | kgs. |
| --- | --- | --- |
| Ground yellow corn | 1242 | 564.5 |
| CLA | 5 | 2.3 |
| Alfalfa meal, 17% | 25 | 11.3 |
| Soybean meal, dehulled | 451.6 | 205.3 |
| Meat and bone meal (47%) | 50 | 23.0 |
| DL-methionine | 1.0 | .5 |
| Dicalcium phosphate | 7 | 3.1 |
| Ground limestone | 174 | 79.1 |
| Iodized salt | 7 | 3.1 |
| Stabilized yellow grease | 37 | 17.2 |
| Mineral and vitamin supplements | | |
| Calcium pantothenate (mg) | 5,000 | |
| Manganese (g) | 52 | |
| Selenium (mg) | 90.8 | |
| Zinc (g) | 16 | |
| Vitamin A (IU) | 6,000,000 | |
| Vitamin D$_3$ (IU) | 2,000,000 | |
| Choline (mg) | 274,000 | |
| Niacin (mg) | 12,000 | |

TABLE 21-continued

| Ingredients | lbs. | kgs. |
| --- | --- | --- |
| Riboflavin (mg) | 2,000 | |
| Vitamin B-12 | 6 | |
| Total | 2000 | 909.4 |

E. Starter and Finisher Rations for Broilers

TABLE 22

| | Starter (up to 24 days) | | Finisher (25 days to market) | |
| --- | --- | --- | --- | --- |
| Ingredients | lbs. | kgs. | lbs. | kgs. |
| Ground yellow corn | 1,106 | 503 | 1235 | 561 |
| CLA-ester | 5 | 2.3 | 5 | 2.3 |
| Soybean meal, dehulled | 605 | 275 | 420 | 191 |
| Alfalfa meal, 17% | — | — | 25 | 11 |
| Corn gluten meal, 60% | 50 | 23 | 75 | 34 |
| Fish meal, herring, 65% | 50 | 23 | 50 | 23 |
| Meat and bone meal, 47% | 50 | 23 | 50 | 23 |
| Dicalcium phosphate | 10 | 4 | 9 | 4 |
| Ground limestone | 16 | 7 | 14 | 6.3 |
| DL-methionine | 0.8 | 0.3 | — | — |
| Stabilized yellow grease | 101 | 45.7 | 110 | 49.4 |
| Iodized salt | 7 | 3 | 7 | 3 |
| Mineral and vitamin supplement | | | | |
| Calcium pantothenate (mg) | 5,000 | | 5,000 | |
| Manganese (g) | 75 | | 75 | |
| Organic arsenical supplement | 0.1 | | 0.1 | |
| Selenium (mg) | 90.8 | | 90.8 | |
| Zinc (g) | 30 | | 30 | |
| Vitamin A (IU) | 4,000,000 | | 4,000,000 | |
| Vitamin D (IU) | 1,000,000 | | 1,000,000 | |
| Vitamin E (mg) | 2,000 | | 2,000 | |
| Vitamin K (mg) | 2,000 | | 2,000 | |
| Choline (mg) | 503,000 | | 672,000 | |
| Niacin (mg) | 20,000 | | 20,000 | |
| Riboflavin (mg) | 3,000 | | 3,000 | |
| Vitamin B-12 (mg) | 12 | | 12 | |
| Total | 2000.9 | 909.3 | 2000.1 | 909.5 |

F. Grower/Finisher Turkey Rations

TABLE 23

| | Grower (8-16 weeks) | | Finisher (16 weeks-market) | |
| --- | --- | --- | --- | --- |
| Ingredients | lbs. | kgs. | lbs. | kgs. |
| Ground yellow corn | 1194 | 595 | 1490 | 677.2 |
| Wheat middlings | 50 | 23 | — | — |
| Alfalfa meal, 17% | 25 | 11.3 | 25 | 11.3 |
| Soybean meal, dehulled | 570 | 259 | 335 | 152.3 |
| Meat and bone meal, 47% | 50 | 23 | 50 | 23 |
| Dicalcium phosphate | 32 | 14.5 | 23 | 10.5 |
| Ground limestone | 14 | 6 | 17 | 8 |
| Stabilized yellow grease | 45 | 20.7 | 45 | 20.7 |
| CLA-ester | 5 | 2.3 | 5 | 2.3 |
| Iodized Salt | 10 | 4.5 | 10 | 4.5 |
| Mineral and vitamin supplements | | | | |
| Calcium pantothenate (mg) | 4,500 | | 4,500 | |
| Manganese (g) | 30 | | 30 | |
| Selenium (mg) | 181.6 | | 181.6 | |
| Zinc (g) | 30 | | 30 | |
| Vitamin (IU) | 1,500,000 | | 7,500,000 | |
| Vitamin D (IU) | 1,700,000 | | 1,700,000 | |
| Vitamin E (IU) | 10,000 | | 10,000 | |
| Biotin (mg) | 100 | | 100 | |
| Choline (mg) | 388,000 | | 417,000 | |
| Niacin (mg) | 46,000 | | 48,000 | |

TABLE 23-continued

|  | Grower (8-16 weeks) | | Finisher (16 weeks-market) | |
| --- | --- | --- | --- | --- |
| Ingredients | lbs. | kgs. | lbs. | kgs. |
| Riboflavin (mg) | 5,000 | | 5,000 | |
| Vitamin B-12 | 6 | | 6 | |
| Total | 2000 | 909.3 | 2000 | 909.3 |

G. Dry Dog Food Formula

TABLE 24

| Ingredients | Formula 1, % | Formula 2, % |
| --- | --- | --- |
| Meat and bone meal, 50% CP | 8.0 | 15.0 |
| Fish meal, 60% CP, low fat | 5.0 | 3.0 |
| Soybean meal, 44% CP | 12.0 | — |
| Soybean meal, 50% CP | — | 19.0 |
| Wheat germ meal, 25% CP | 8.0 | 5.0 |
| Skimmed milk, dried | 4.0 | 2.75 |
| Cereal grains, mixed | 51.23 | — |
| Corn, flaked | — | 23.25 |
| Wheat bran | 4.0 | — |
| Wheat, flaked | — | 23.35 |
| Animal fat | 1.75 | 2.75 |
| CLA-ester | .25 | .25 |
| Steamed bone meal | 2.0 | — |
| Brewers yeast | 2.0 | 5.0 |
| Fermentation solubles, dehydrated | 1.0 | — |
| Salt and trace minerals | 0.5 | 0.5 |
| Vitamin mixture | 0.25 | 0.25 |
| Ferric oxide | 0.02 | — |
| Total | 100.00 | 100.00 |

H. Semi-Moist Dog Food Formulas

TABLE 25

| Ingredients | Formula 1, % | Formula 2, % |
| --- | --- | --- |
| Soy flakes | 30.9 | 33.5 |
| Meat byproducts, 70% moisture | 32.0 | — |
| Meat and bone meal, dehydrated | — | 7.3 |
| Water | — | 25.6 |
| Sugar | 21.0 | 21.0 |
| Calcium and phosphorous supplement | 3.3 | — |
| Soybean hulls | 3.1 | 3.1 |
| Skimmed milk, dried | 2.5 | — |
| Propylene glycol | 2.1 | 2.1 |
| Sorbitol | 2.0 | 2.0 |
| Animal fat | .75 | 3.95 |
| CLA-ester | .25 | .25 |
| Emulsifiers | 0.9 | — |
| Potassium sorbate | 0.35 | 0.35 |
| Salt | 0.6 | 0.6 |
| Vitamins | 0.25 | 0.25 |
| Total | 100.000 | 100.000 |

Example 11

Large-Scale Preparation of CLA

This example illustrates a method of preparing free fatty acids of CLA on a pilot scale by the isomerization of safflower oil. 1000 kg of KOH was dissolved in 2070 L of propylene glycol. The mixture was then heated to 100° C. with stirring. Next, 2340 L of safflower oil was added and the temperature was elevated to 150° C. for 3 hours. The mixture was then cooled and 1000 L of water and 1350 L of HCL was added. At this point, the solution separated into two layers, with the free fatty acids as the top layer. The layers were separated and the bottom aqueous layer discarded. The top layer was washed with 1000 L of water containing 50 kg of citric acid. The aqueous layer was discarded and the oil (CLA) containing layer was dried under vacuum.

Example 12

Detection of Volatile Compounds

This example illustrates the detection of volatile organic compounds using head space capillary gas chromatography and mass spectroscopy. Three grams of CLA prepared by the method of Example 11 was purged with nitrogen at 100 ml/min at 70° C. in a sliff tube. Volatile compounds released were absorbed on Tenex GR by the purge and trap technique. The absorbed compounds were then injected by a Perkin Elmer ATD injector on to a Hewlett Packard 5890/5970 GC/MSD gas chromatography system equipped with a wax-ether column (J&W). Peaks were identified using Wiley reference search.

Table 27 shows the most predominant peaks and their relative abundance (area %). Eleven volatile compounds were identified in the sample, including pentane and hexane. Many of these compounds, including hexane are undesirable in products for animal or human consumption. These results demonstrate that CLA samples prepared by chemical conjugation of oils contain undesirable volatile organic compounds.

Example 13

Oxidation of CLA

This example demonstrates the oxidation of CLA over time. CLA was prepared as described in Example 11. One sample was left in a test tube at room temperature for 21 days. A second reference sample was stored at −30° C. The increase in pentane and hexane in both samples was measured by the method described in Example 12. Results are shown in Table 28. The amount of both pentane and hexane present in the sample increased by approximately two-fold after 21 days of storage at room temperature. This example demonstrated that CLA samples prepared by chemical conjugation of oils oxidize over time to form undesirable volatile organic compounds.

Example 14

Production of Triacylglycerides

CLA was prepared according to the method of Example 11. The product was then distilled on a molecular distillation plant at 150° C. and a pressure of $10^{-2}$ mbar. Next, 1000 kg of the distilled product was mixed with 97 kg of pure glycerol and 80 kg lipase. The reaction was allowed to proceed for 12 hours at 55° C. under vacuum and with stirring. The triacylglyceride product was distilled on a molecular distillation apparatus to remove unreacted fatty acids.

Example 15

Oxidation of CLA Triacylglycerides

Aliquots of the product of Example 14 were placed in open dishes and stored under controlled conditions at 60° C. Antioxidants were added to some of the samples in varying amounts. Antioxidants used were Controx (Grunau (Henkel), Illertissen, DE), Herbalox (Kalsec, Kalamazoo, Mich.), Covi-OX (Grunau (Henkel), Illertissen, DE), and alpha-tocopherol. Antioxidants were added at 0, 0.02, 0.05, and 0.10% by weight.

The oxygen stability index (OSI) was measured using a method known in the art (AOCS official method Cd 12b-92 using an OSI apparatus from Omnion Instruments). Samples (5 g) were held in a thermostable bath and a stream of purified air was passed through the samples. The effluent air from the samples was bubbled through a vessel containing deionized water. The conductivity of the water is continually monitored over time. The OSI (the point of maximum change of the rate of oxidation) is determined mathematically. Results of the OSI measurements are shown in Table 29 and FIG. 2. The addition of alpha-tocopherol did not significantly increase the OSI value. Herbalox increased the value by approximately 2-3 fold. Covi-OX and Controx increased the OSI values by a greater amount, approximately 4 and 6 fold, respectively. This experiment demonstrated that the addition of certain antioxidants containing metal oxidant chelators can slow the oxidation of CLA containing compounds during storage.

Example 16

Treatment with Absorbing Agents

A triacyglyceride of CLA was prepared as described in Example 14. The sample was deodorized at 150° C. and 1 mm Hg for 3 hours. Next, 500 ml of the sample was treated with powdered silica. Silica was added to 2% and heated to 90-100° C. under vacuum for 30 minutes. The sample was then cooled and filtered.

TABLE 26

| Retention Time | Area % | Volatile Compound |
|---|---|---|
| 2.33 | 0.43 | Pentane |
| 2.52 | 0.64 | Hexane |
| 2.93 | 0.66 | Heptane |
| 5.65 | 0.75 | 2-Butenal |
| 7.35 | 16.44 | Ethanol |
| 8.81 | 5.85 | 3-Methyl Butanal |
| 9.72 | 1.32 | 4-Methyl Pentanone |
| 12.29 | 16.04 | Hexanal |
| 15.55 | 8.26 | Heptanal |
| 16.63 | 1.29 | 2-Pentyl Furan |
| 18.03 | 2.56 | Octanal |

TABLE 27

| Volatile Compound | Day zero (GC area × 1E6) | Day 21 (GC area × 1E6) |
|---|---|---|
| Pentane | 52 | 105 |
| Hexane | 94 | 192 |

TABLE 28

OSI Values in the presence of antioxidants (standard deviation)

| Weight % | Controx | Herbalox | Covi-OX | alpha-tocopherol |
|---|---|---|---|---|
| 0.00 | 24.27 (1.78) | 25.80 (4.88) | 25.40 (5.69) | 24.23 (3.32) |
| 0.02 | 62.85 (1.24) | 26.23 (1.37) | 52.00 (2.73) | 30.40 (2.02) |
| 0.05 | 109.92 (2.38) | 41.62 (1.71) | 74.68 (8.00) | 38.97 (3.13) |
| 0.10 | 161.50 (2.83) | 66.95 (1.99) | 111.38 (2.83) | 40.47 (0.86) |

Example 17

Production of CLA with Alcoholate Catalysts

This example describes the production of CLA from safflower oil using potassium methylate as a catalyst. Distilled methyl ester of sunflower oil (41.5 g) was placed in a reactor with 0.207 g methanol and 0.62 g potassium methylate, and the reactor purged with nitrogen before closing. The contents of the reactor were stirred while to 120° C. The reaction was then allowed to proceed at 120° C. for 4 hours. the reactor was then cooled to 80° C. and the contents were transferred to a separating funnel and washed with hot distilled water and then with hot water containing citric acid. The methylester was then dried under vacuum with moderate heat. The dried methyl ester was dissolved in isooctane and analyzed by GLC with a Perkin Elmer autosampler. The column was a highly polar fused silica type. the following program was used:

| | |
|---|---|
| Injection: | Splitless at 250° C. |
| Detection: | Flame ionization detector at 280° C. |
| Carrier: | Helium at psig. |
| Oven program: | 80° C.-130° C. (45° C./min.), then 1° C./min. to 220° C. and 220° C. throughout for 10 min. |
| Column: | WCOT FUSED SILICA 0.25 mm 100 m, CP-SIL 88 for FAME, df + 0.2. |

The CLA obtained consisted almost exclusively of the c9,t11 and t10,c12 isomers of CLA as shown in Table 30.

TABLE 29

CLA Produced by Isomerization with Potassium-Methylate

| Fatty Acid | Before Isomerization | After Isomerization |
|---|---|---|
| C 16:0 | 5.41 | 5.54 |
| C 18:0 | 3.87 | 3.72 |
| C 18:1 | 29.01 | 29.19 |
| C 18:2, c9,c12 | 59.43 | 0.84 |
| CLA, c9,c11 | 0 | 28.84 |
| CLA, t10,c12 | 0 | 28.45 |
| CLA, c9,c11 | 0 | 0.56 |
| CLA, c10,c12 | 0 | 0.40 |
| CLA, t9,t11; t10,t12 | 0 | 0.27 |

Example 18

Products Formed by Conjugation of Linolenic Acid

This example describes the products formed by conjugation of linolenic acid. Pure linolenic acid (Nu Check Prep.) was esterified and 1.08 grams of the fatty acid methyl ester of linolenic was mixed with 43.0 mg of potassium methylate together with 10.8 mg methanol in a test tube. The test tube was purged with nitrogen and closed. A magnetic bar was used for stirring the mixture. The reaction was allowed to proceed at 120° C. for 3 hours. The sample was washed twice with water and once with citric acid and diluted into isooctane for GLC analysis. The conditions were the same as in example 17, except for the oven program and the column:

| | |
|---|---|
| Oven program: | 80° C.-160° C. (25° C./min.), then 5° C./min. to 220° C. and 220° C. throughout for 10 min. |
| Column: | WCOT FUSED SILICA 0.25 mm 100 m, CP-SIL 5CB for FAME, df + 0.12. |

The results (Table 31) demonstrate the existence of seven peaks of 1% or more. Each of these peaks represents acids with 2 or 3 bonds in the conjugated position. It is not known if the fatty acids corresponding to these peaks are found in nature and their possible effects are not known.

TABLE 30

Relative Area Percentage of Unknown Isomers of Conjugated Linolenic Acid

| Fatty Acid | Before Conjugation | After Conjugation |
|---|---|---|
| C 18:3 | 99.53 | 2.43 |
| unknown | 0 | 55.82 |
| unknown | 0 | 0.98 |
| unknown | 0 | 2.03 |
| unknown | 0 | 3.79 |
| unknown | 0 | 4.7 |
| unknown | 0 | 5.17 |
| unknown | 0 | 20.74 |

Example 19

CLA Oxidation Products

This example describes the oxidation of CLA exposed to open air. A small sample of methyl ester was prepared and stored in an open test tube for 115 days at room temperature with free access to air. The CLA initially present in the sample was completely broken down and transformed into furan fatty acids and other unidentified derivatives. The relative content of the CLA sample before and after oxidation is shown in Table 3. This chromatogram shows only relatively non-polar components. A chromatogram of the same sample was also run on a polar column. The results indicated the presence of a large number of short chain polar components (i.e., breakdown products).

TABLE 31

CLA Composition Before and After Oxidation in Open Test Tube for 115 days

| Fatty Acid | Day 0 | Day 115 |
|---|---|---|
| C 16:0 | 1.36 | 1027 |
| C18:1, t9 | 0 | 0.33 |
| C18:1, c9 | 4.14 | 3.19 |
| C18:1, c11 | 0.13 | 0.10 |
| Unknown | 0 | 0.21 |
| C18:2, c9,c12 | 0.06 | 0.03 |
| CLA, c9,t11 | 7.68 | 0 |
| CLA, t10,c12 | 7.63 | 0 |
| CLA, c9,c11 | 0.11 | 0 |
| CLA, c10,c12 | 0.09 | 0 |
| CLA, t9,t11; t10,t12 | 0.06 | trace |
| Unknown | 0 | 0.26 |
| Unknown | 0 | 0.26 |
| Unknown | 0.16 | 0.14 |

What should be clear from above is that the present invention provides a conjugated linoleic acid composition of high purity that can be used in the formulation of animal feeds and in food products suitable for human consumption.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in medicine, biochemistry, or related fields are intended to be within the scope of the following claims.

The invention claimed is:

1. A composition comprising an isomerized conjugated linoleic acid composition containing less than 1% total 8,10 octadecadienoic acids, 11,13 octadecadienoic acids, and trans-trans octadecadienoic acids and less than 100 parts per million total of volatile organic compounds.

2. The composition of claim 1, wherein said isomerized conjugated linoleic acid composition comprises free fatty acids.

3. The composition of claim 1, wherein said isomerized conjugated linoleic acid composition comprises alkyl esters.

4. The composition of claim 1, wherein said isomerized conjugated linoleic acid composition comprises triacylglycerides.

5. The composition of claim 1, wherein said composition further comprises a metal oxidant chelator.

6. The composition of claim 5, wherein said metal oxidant chelator is selected from the group consisting of citric acid esters and lecithin.

7. The composition of claim 1, wherein said composition contains less than 50 parts per million total of volatile organic compounds.

8. The composition of claim 1, wherein said composition contains less than 10 parts per million total of volatile organic compounds.

9. The composition of claim 1, wherein said composition contains less than 5 parts per million total of volatile organic compounds.

10. A food product comprising an isomerized conjugated linoleic acid composition containing less than 1% total 8,10 octadecadienoic acids, 11,13 octadecadienoic acids, and trans-trans octadecadienoic acids and an metal oxidant chelator, wherein said isomerized conjugated linoleic acid composition contains less than 100 parts per million total of volatile organic compounds.

11. The food product of claim 10, wherein said conjugated linoleic acid is provided as a moiety selected from the group consisting of a triacylglyceride, a free fatty acid, and an alkyl ester.

12. The food product of claim 10, wherein said isomerized conjugated linoleic acid composition contains less than 50 parts per million total of volatile organic compounds.

13. The food product of claim 10, wherein said isomerized conjugated linoleic acid composition contains less than 10 parts per million total of volatile organic compounds.

14. The food product of claim 10, wherein said isomerized conjugated linoleic acid composition contains less than 5 parts per million total of volatile organic compounds.

15. A food supplement comprising a isomerized conjugated linoleic acid composition containing less than 1% total 8,10 octadecadienoic acids, 11,13 octadecadienoic acids, and trans-trans octadecadienoic acids and an metal oxidant chelator, wherein said isomerized conjugated linoleic acid composition contains less than 100 parts per million total of volatile organic compounds.

16. The food supplement of claim 15, wherein said conjugated linoleic acid is provided as a moiety selected from the group consisting of a triacylglyceride, a free fatty acid, and an alkyl ester.

17. The food supplement of claim 15, wherein said isomerized conjugated linoleic acid composition contains less than 50 parts per million total of volatile organic compounds.

18. The food supplement of claim 15, wherein said isomerized conjugated linoleic acid composition contains less than 10 parts per million total of volatile organic compounds.

19. The food supplement of claim 15, wherein said isomerized conjugated linoleic acid composition contains less than 5 parts per million total of volatile organic compounds.

20. A method comprising
   a. providing a seed oil containing seed oil;
   b. isomerizing said linoleic acid to form a conjugated linoleic acid composition containing less than 1% total 8,10 octadecadienoic acids, 11,13 octadecadienoic acids, and trans-trans octadecadienoic acids; and
   c. treating said conjugated linoleic acid composition under conditions such that said composition contains less than 100 parts per million of volatile organic compounds.

21. The method of claim 20, wherein said conjugated linoleic acid composition contains less than 50 parts per million of volatile organic compounds.

22. The method of claim 20, wherein said conjugated linoleic acid composition contains less than 10 parts per million of volatile organic compounds.

23. The method of claim 20, wherein said conjugated linoleic acid composition contains less than 5 parts per million of volatile organic compounds.

24. A food product comprising a conjugated linoleic acid composition containing less than 1% total 8,10 octadecadienoic acids, 11,13 octadecadienoic acids, and trans-trans octadecadienoic acids and a metal oxidant chelator.

25. The food product of claim 24, wherein said metal oxidant chelator is selected from lecithin and ascorbic acid.

26. The food product of claim 24, wherein said conjugated linoleic acid composition contains less than 100 ppm volatile organic compounds.

27. The food product of claim 24, wherein said conjugated linoleic acid composition contains less than 5 ppm volatile organic compounds.

28. The food product of claim 24, wherein said conjugated linoleic acid composition comprises esters of conjugated linoleic acid.

29. The food product of claim 24, wherein said conjugated linoleic acid composition comprises triglycerides containing conjugated linoleic acid.

30. The food product of claim 24, wherein said conjugated linoleic acid composition comprises free fatty acids.

31. A food product comprising an isomerized conjugated linoleic acid composition containing less than 1% total 8,10 octadecadienoic acids, 11,13 octadecadienoic acids, and trans-trans octadecadienoic acids, said conjugated linoleic acid composition having a sufficiently low volatile organic compound concentration so that the taste and smell of said food product is not affected.

32. The food product of claim 31, wherein said conjugated linoleic acid composition comprises alkyl esters.

33. The food product of claim 31, wherein said conjugated linoleic acid composition comprises free fatty acids.

34. The food product of claim 31, wherein said conjugated linoleic acid composition comprises triglycerides.

35. A composition comprising an isomerized conjugated linoleic acid composition containing less than 1% total 8,10 octadecadienoic acids, 11,13 octadecadienoic acids, and trans-trans octadecadienoic acids, said conjugated linoleic acid composition having a sufficiently low volatile organic compound concentration so that the taste and smell of said composition is not affected.

36. The composition of claim 35, wherein said conjugated linoleic acid composition comprises alkyl esters.

37. The composition of claim 35, wherein said conjugated linoleic acid composition comprises free fatty acids.

38. The composition of claim 35, wherein said conjugated linoleic acid composition comprises triglycerides.

* * * * *